(12) United States Patent
Cox et al.

(10) Patent No.: US 8,921,534 B2
(45) Date of Patent: Dec. 30, 2014

(54) ENHANCEMENT OF THE IMMUNE RESPONSE USING CD36-BINDING DOMAIN

(75) Inventors: William I. Cox, East Greenbush, NY (US); Jeannine P. Alexander, Clifton Park, NY (US); Scott Goebel, Ballston Spa, NY (US)

(73) Assignee: Sanofi Pasteur Limited

( * ) Notice: Subject to any disclaimer, the term of this patent is extended or adjusted under 35 U.S.C. 154(b) by 0 days.

(21) Appl. No.: 10/317,821

(22) Filed: Dec. 12, 2002

(65) Prior Publication Data

US 2004/0241652 A1 Dec. 2, 2004

Related U.S. Application Data

(60) Provisional application No. 60/341,771, filed on Dec. 12, 2001.

(51) Int. Cl.
*C07H 21/04* (2006.01)

(52) U.S. Cl.
USPC ........................................ 536/23.1; 536/23.4

(58) Field of Classification Search
None
See application file for complete search history.

(56) References Cited

U.S. PATENT DOCUMENTS

| | | | |
|---|---|---|---|
| 5,174,993 A | 12/1992 | Paoletti | |
| 5,185,146 A | 2/1993 | Altenburger | |
| 5,274,087 A | 12/1993 | Barnett | |
| 5,348,887 A | 9/1994 | Bumol | |
| 5,364,773 A | 11/1994 | Paoletti | |
| 5,494,807 A | 2/1996 | Paoletti | |
| 5,571,710 A | 11/1996 | Barnett | |
| 5,698,530 A | 12/1997 | Schlom | |
| 5,698,679 A | 12/1997 | Nemazee | |
| 5,756,103 A | 5/1998 | Paoletti | |
| 5,766,599 A | 6/1998 | Paoletti | |
| 5,833,975 A | 11/1998 | Paoletti | |
| 5,990,091 A | 11/1999 | Tartaglia | |
| 6,045,802 A | 4/2000 | Schlom | |
| 6,071,716 A | 6/2000 | Freeman | |
| 6,224,870 B1 | 5/2001 | Segal | |
| 6,294,381 B1 | 9/2001 | Olweus | |
| 6,964,763 B1 * | 11/2005 | Crombie et al. | 424/94.1 |
| 7,220,557 B2 * | 5/2007 | Hastings et al. | 435/69.1 |
| 2001/0041670 A1 | 11/2001 | Simantov | |
| 2003/0092900 A1 | 5/2003 | Iruela-Arispe | |
| 2006/0269960 A1 | 11/2006 | Knuth | |
| 2008/0177031 A1 | 7/2008 | Jager | |

FOREIGN PATENT DOCUMENTS

| | | |
|---|---|---|
| WO | WO9113157 A1 | 9/1991 |
| WO | WO9221376 A1 | 12/1992 |
| WO | WO9306848 A1 | 4/1993 |
| WO | WO9858956 A2 | 12/1998 |
| WO | WO 99/37660 * | 7/1999 |
| WO | WO9937660 A1 | 7/1999 |
| WO | WO9940188 A2 | 8/1999 |
| WO | WO03050268 A3 | 6/2003 |

OTHER PUBLICATIONS

Crombie et al. J. Exp. Med., 1998, vol. 187, p. 25-35.*
Database EMBL-X14878.*
Ivanoff, et al. V3 Loop Region of the HIV-1 gp120 Envelope Protein Is Essential for Virus Infectivity. Virology, 187, pp. 423-432 (1992).
Albert, ML, et al. Immature dendritic cells phagocytose apoptotic cells via alphavbeta5 and CD36, and cross-present antigens to cytotoxic T lymphocytes. J. Exp. Med. vol. 188: 1359-1368 (1998).
Asch, A.S., et al., "Thrombospondin sequence motif (CSVTCG) is responsible for CD36 binding." Biochem. Biophys. Res. Commun. vol. 182: 1208-1217 (1992).
Carron, et al. A CD36-Binding Peptide from Thrombospondin-1 Can Stimulate Resorption by Osteoclasts in Vitro. Biochem. Biophys. Res. Commun. vol. 270: 1124-1127 (2000).
Crombie, et al. Identification of a CD36-related Thrombospondin 1-binding Domain in HIV-1 Envelope Glycoprotein gp120: Relationship to HIV-1-specific Inhibitory Factors in Human Saliva. J. Exp. Med. vol. 187(1): 25-35 (Jan. 5, 1998).
Gao, et al. Genetic Variation of HIV Type I in Four World Health Organization-Sponsored Vaccine Evaluation Site: Generation of Functional Envelope (Glycoprotein 160) Clones Representative of Sequence Subtypes A, B, C, and E. Aids Res. Human Ret. vol. 10(11): 1359-1368 (1994).
Li, W., et al. Identification of SVTCG in Thrombospondin as the Conformation-dependent, High Affinity Binding Site for Its Receptor, CD36. J. Biol. Chem. vol. 268: 16179-16184 (1993).
Magnetto, S., et al. CD36 mediates binding of soluble thrombospondin-1 but not cell adhesion and haptotaxis on immobilized thrombospondin-1. Cell Biochem. Funct., 16(3): 211 (1998).
Mulligan, R. The basic science of gene therapy. Science, 260 (5110): 926-32 (1993).
Pearce, et al. Recombinant GST/CD36 Fusion Proteins Define a Thrombospondin Binding Domain. J. Biol. Chem. vol. 270(7): 2981-2986 (1995).
Pearce, et al. Recombinant Glutathione S-Transferase/CD36 Fusion Proteins Define an Oxidized Low Density Lipoprotein-binding Domain. J. Biol. Chem. vol. 273(52): 34875-34881 (1998).
Robinson et al. Protection against a lethal influenza virus challenge by immunization with a haemagglutinin-expressing plasmid DNA. Vaccine, vol. 11: 957 (1993).
Shiver et al. Anti-HIV env immunities elicited by nucleic acid vaccines. Vaccine, vol. 15: 884 (1997).
Stern et al., "Human monocyte-derived macrophage phagocytosis of eosinophils undergoing apoptosis. Mediation by alpha v beta 3/CD36/thrombospondin recognition mechanisms and lack phlogistic response," Am. J. Pathol. 149 (3):911 (1996).

(Continued)

*Primary Examiner* — Yunsoo Kim
(74) *Attorney, Agent, or Firm* — Patrick J. Halloran; Reza Yacoub

(57) ABSTRACT

The invention relates to reagents and methods for enhancing an immune response using CD36 binding region/antigen hybrid polypeptides or polynucleotides encoding the hybrid polypeptides.

13 Claims, 19 Drawing Sheets

(56) References Cited

OTHER PUBLICATIONS

Figure 1A:
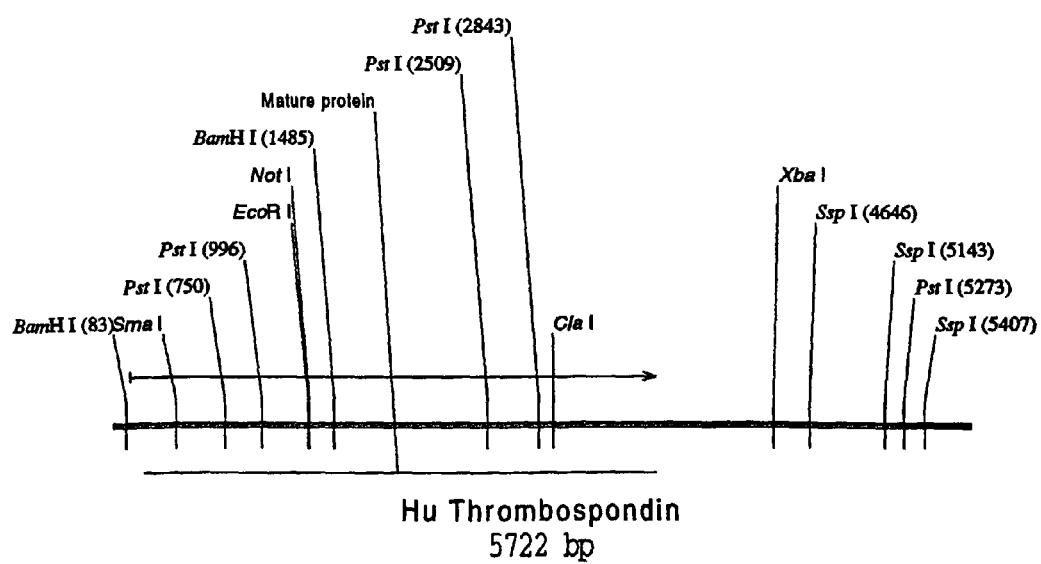

Tartaglia, et al. Protection of Cats against Feline Leukemia Virus by Vaccination with a Canarypox Virus Recombinant, ALVAC-FL. J. Virol. vol. 67: 2370 (1993).

Ulmer et al. Expession and immunogenecity of Mycobacterium tuberculosis antigen 85 by DNA vaccination. Vaccine, vol. 15: 792 (1997).

Hennessy, et al. GenBank Accession No. X14787, 1989.

* cited by examiner

FIGURE 1B

```
  1  GGACGCACAG GCATTCCCCG CGCCCCTCCA GCCCTCGCCG CCCTCGCCAC
     CCTGCGTGTC CGTAAGGGGC GCGGGGAGGT CGGGAGCGGC GGGAGCGGTG
                                            BamHI
                                            ------
 51  CGCTCCCGGC CGCCGCGCTC CGGTACACAC AGGATCCCTG CTGGGCACCA
     GCGAGGGCCG GCGGCGCGAG GCCATGTGTG TCCTAGGGAC GACCCGTGGT

+1                       MetGlyLeu AlaTrpGlyLeu GlyValLeu PheLeuMet
                          ]------------------------------------------
101  ACAGCTCCAC CATGGGGCTG GCCTGGGGAC TAGGCGTCCT GTTCCTGATG
     TGTCGAGGTG GTACCCCGAC CGGACCCCTG ATCCGCAGGA CAAGGACTAC

+1  HisValCysGly ThrAsnArg IleProGlu SerGlyGlyAsp AsnSerVa
     -------------------------------------------------------
151  CATGTGTGTG GCACCAACCG CATTCCAGAG TCTGGCGGAG ACAACAGCGT
     GTACACACAC CGTGGTTGGC GTAAGGTCTC AGACCGCCTC TGTTGTCGCA

+1  lPheAspIle PheGluLeuThr GlyAlaAla ArgLysGly SerGlyArgA
     -------------------------------------------------------
201  GTTTGACATC TTTGAACTCA CCGGGGCCGC CCGCAAGGGG TCTGGGCGCC
     CAAACTGTAG AAACTTGAGT GGCCCCGGCG GGCGTTCCCC AGACCCGCGG

+1  rgLeuValLys GlyProAsp ProSerSerPro AlaPheArg IleGluAsp
     -------------------------------------------------------
251  GACTGGTGAA GGGCCCCGAC CCTTCCAGCC CAGCTTTCCG CATCGAGGAT
     CTGACCACTT CCCGGGGCTG GGAAGGTCGG GTCGAAAGGC GTAGCTCCTA

+1  AlaAsnLeuIle ProProVal ProAspAsp LysPheGlnAsp LeuValAs
     -------------------------------------------------------
301  GCCAACCTGA TCCCCCCTGT GCCTGATGAC AAGTTCCAAG ACCTGGTGGA
     CGGTTGGACT AGGGGGGACA CGGACTACTG TTCAAGGTTC TGGACCACCT

+1  pAlaValArg AlaGluLysGly PheLeuLeu LeuAlaSer LeuArgGlnM
     -------------------------------------------------------
351  TGCTGTGCGG GCAGAAAAGG GTTCCTCCT TCTGGCATCC CTGAGGCAGA
     ACGACACGCC CGTCTTTTCC CAAAGGAGGA AGACCGTAGG GACTCCGTCT

+1  etLysLysThr ArgGlyThr LeuLeuAlaLeu GluArgLys AspHisSer
     -------------------------------------------------------
                  SmaI
                  ------
401  TGAAGAAGAC CCGGGGCACG CTGCTGGCCC TGGAGCGGAA AGACCACTCT
     ACTTCTTCTG GGCCCCGTGC GACGACCGGG ACCTCGCCTT TCTGGTGAGA

+1  GlyGlnValPhe SerValVal SerAsnGly LysAlaGlyThr LeuAspLe
     -------------------------------------------------------
451  GGCCAGGTCT TCAGCGTGGT GTCCAATGGC AAGGCGGGCA CCCTGGACCT
     CCGGTCCAGA AGTCGCACCA CAGGTTACCG TTCCGCCCGT GGGACCTGGA

+1  uSerLeuThr ValGlnGlyLys GlnHisVal ValSerVal GluGluAlaL
     -------------------------------------------------------
501  CAGCCTGACC GTCCAAGGAA AGCAGCACGT GGTGTCTGTG GAAGAAGCTC
     GTCGGACTGG CAGGTTCCTT TCGTCGTGCA CCACAGACAC CTTCTTCGAG

+1  euLeuAlaThr GlyGlnTrp LysSerIleThr LeuPheVal GlnGluAsp
     -------------------------------------------------------
551  TCCTGGCAAC CGGCCAGTGG AAGAGCATCA CCCTGTTTGT GCAGGAAGAC
     AGGACCGTTG GCCGGTCACC TTCTCGTAGT GGGACAAACA CGTCCTTCTG
```

FIGURE 1C

```
     +1  ArgAlaGlnLeu TyrIleAsp CysGluLys MetGluAsnAla GluLeuAs
         ----------------------------------------------------
   601   AGGGCCCAGC TGTACATCGA CTGTGAAAAG ATGGAGAATG CTGAGTTGGA
         TCCCGGGTCG ACATGTAGCT GACACTTTTC TACCTCTTAC GACTCAACCT
. . . . . . . . . . . . . . . . . . . . . . . . . . . . . . .
     +1  pValProIle GlnSerValPhe ThrArgAsp LeuAlaSer IleAlaArgL
         ----------------------------------------------------
   651   CGTCCCCATC CAAAGCGTCT TCACCAGAGA CCTGGCCAGC ATCGCCAGAC
         GCAGGGGTAG GTTTCGCAGA AGTGGTCTCT GGACCGGTCG TAGCGGTCTG
. . . . . . . . . . . . . . . . . . . . . . . . . . . . . . .
     +1  euArgIleAla LysGlyGly ValAsnAspAsn PheGlnGly ValLeuGln
                                                          PstI
                                                         ------
   701   TCCGCATCGC AAAGGGGGGC GTCAATGACA ATTCCAGGG GGTGCTGCAG
         AGGCGTAGCG TTTCCCCCCG CAGTTACTGT TAAAGGTCCC CCACGACGTC
. . . . . . . . . . . . . . . . . . . . . . . . . . . . . . .
     +1  AsnValArgPhe ValPheGly ThrThrPro GluAspIleLeu ArgAsnLy
         ----------------------------------------------------
   751   AATGTGAGGT TTGTCTTTGG AACCACACCA GAAGACATCC TCAGGAACAA
         TTACACTCCA AACAGAAACC TTGGTGTGGT CTTCTGTAGG AGTCCTTGTT
. . . . . . . . . . . . . . . . . . . . . . . . . . . . . . .
     +1  sGlyCysSer SerSerThrSer ValLeuLeu ThrLeuAsp AsnAsnValV
         ----------------------------------------------------
   801   AGGCTGCTCC AGCTCTACCA GTGTCCTCCT CACCCTTGAC AACAACGTGG
         TCCGACGAGG TCGAGATGGT CACAGGAGGA GTGGGAACTG TTGTTGCACC
. . . . . . . . . . . . . . . . . . . . . . . . . . . . . . .
     +1  alAsnGlySer SerProAla IleArgThrAsn TyrIleGly HisLysThr
         ----------------------------------------------------
   851   TGAATGGTTC CAGCCCTGCC ATCCGCACTA ACTACATTGG CCACAAGACA
         ACTTACCAAG GTCGGGACGG TAGGCGTGAT TGATGTAACC GGTGTTCTGT
. . . . . . . . . . . . . . . . . . . . . . . . . . . . . . .
     +1  LysAspLeuGln AlaIleCys GlyIleSer CysAspGluLeu SerSerMe
         ----------------------------------------------------
   901   AAGGACTTGC AAGCCATCTG CGGCATCTCC TGTGATGAGC TGTCCAGCAT
         TTCCTGAACG TTCGGTAGAC GCCGTAGAGG ACACTACTCG ACAGGTCGTA
. . . . . . . . . . . . . . . . . . . . . . . . . . . . . . .
     +1  tValLeuGlu LeuArgGlyLeu ArgThrIle ValThrThr LeuGlnAspS
                                                          PstI
                                                         ------
   951   GGTCCTGGAA CTCAGGGGCC TGCGCACCAT TGTGACCACG CTGCAGGACA
         CCAGGACCTT GAGTCCCCGG ACGCGTGGTA ACACTGGTGC GACGTCCTGT
. . . . . . . . . . . . . . . . . . . . . . . . . . . . . . .
     +1  erIleArgLys ValThrGlu GluAsnLysGlu LeuAlaAsn GluLeuArg
         ----------------------------------------------------
  1001   GCATCCGCAA AGTGACTGAA GAGAACAAAG AGTTGGCCAA TGAGCTGAGG
         CGTAGGCGTT TCACTGACTT CTCTTGTTTC TCAACCGGTT ACTCGACTCC
. . . . . . . . . . . . . . . . . . . . . . . . . . . . . . .
     +1  ArgProProLeu CysTyrHis AsnGlyVal GlnTyrArgAsn AsnGluGl
         ----------------------------------------------------
  1051   CGGCCTCCCC TATGCTATCA CAACGGAGTT CAGTACAGAA ATAACGAGGA
         GCCGGAGGGG ATACGATAGT GTTGCCTCAA GTCATGTCTT TATTGCTCCT
. . . . . . . . . . . . . . . . . . . . . . . . . . . . . . .
     +1  uTrpThrVal AspSerCysThr GluCysHis CysGlnAsn SerValThrI
         ----------------------------------------------------
  1101   ATGGACTGTT GATAGCTGCA CTGAGTGTCA CTGTCAGAAC TCAGTTACCA
         TACCTGACAA CTATCGACGT GACTCACAGT GACAGTCTTG AGTCAATGGT
```

FIGURE 1D

```
      +1 leCysLysLys ValSerCys ProIleMetPro CysSerAsn AlaThrVal
         ----------- --------- ------------ --------- ---------
    1151 TCTGCAAAAA GGTGTCCTGC CCCATCATGC CCTGCTCCAA TGCCACAGTT
         AGACGTTTTT CCACAGGACG GGGTAGTACG GGACGAGGTT ACGGTGTCAA
         . . . . . . . . . . . . . . . . . . . . . . . . . . .

+1 ProAspGlyGlu CysCysPro ArgCysTrp ProSerAspSer AlaAspAs
         ------------ --------- --------- ------------ --------
    1201 CCTGATGGAG AATGCTGTCC TCGCTGTTGG CCCAGCGACT CTGCGGACGA
         GGACTACCTC TTACGACAGG AGCGACAACC GGGTCGCTGA GACGCCTGCT
         . . . . . . . . . . . . . . . . . . . . . . . . . . .

+1 pGlyTrpSer ProTrpSerGlu TrpThrSer CysSerThr SerCysGlyA
         ---------- ------------ --------- --------- ----------
    1251 TGGCTGGTCT CCATGGTCCG AGTGGACCTC CTGTTCTACG AGCTGTGGCA
         ACCGACCAGA GGTACCAGGC TCACCTGGAG GACAAGATGC TCGACACCGT
         . . . . . . . . . . . . . . . . . . . . . . . . . . .

+1 snGlyIleGln GlnArgGly ArgSerCysAsp SerLeuAsn AsnArgCys
         ----------- --------- ------------ --------- ---------
            EcoRI       NotI
            -----       ----
    1301 ATGGAATTCA GCAGCGCGGC CGCTCCTGCG ATAGCCTCAA CAACCGATGT
         TACCTTAAGT CGTCGCGCCG GCGAGGACGC TATCGGAGTT GTTGGCTACA
         . . . . . . . . . . . . . . . . . . . . . . . . . . .

+1 GluGlySerSer ValGlnThr ArgThrCys HisIleGlnGlu CysAspLy
         ------------ --------- --------- ------------ --------
    1351 GAGGGCTCCT CGGTCCAGAC ACGGACCTGC CACATTCAGG AGTGTGACAA
         CTCCCGAGGA GCCAGGTCTG TGCCTGGACG GTGTAAGTCC TCACACTGTT
         . . . . . . . . . . . . . . . . . . . . . . . . . . .

+1 sArgPheLys GlnAspGlyGly TrpSerHis TrpSerPro TrpSerSerC
         ---------- ------------ --------- --------- ----------
    1401 AAGATTTAAA CAGGATGGTG GCTGGAGCCA CTGGTCCCCG TGGTCATCTT
         TTCTAAATTT GTCCTACCAC CGACCTCGGT GACCAGGGGC ACCAGTAGAA
         . . . . . . . . . . . . . . . . . . . . . . . . . . .

+1 ysSerValThr CysGlyAsp GlyValIleThr ArgIleArg LeuCysAsn
         ----------- --------- ------------ --------- ---------
                                                      BamHI
                                                      -----
    1451 GTTCTGTGAC ATGTGGTGAT GGTGTGATCA CAAGGATCCG GCTCTGCAAC
         CAAGACACTG TACACCACTA CCACACTAGT GTTCCTAGGC CGAGACGTTG
         . . . . . . . . . . . . . . . . . . . . . . . . . . .

+1 SerProSerPro GlnMetAsn GlyLysPro CysGluGlyGlu AlaArgGl
         ------------ --------- --------- ------------ --------
    1501 TCTCCAGCC CCCAGATGAA TGGGAAACCC TGTGAAGGCG AAGCGCGGA
         AGAGGGTCGG GGGTCTACTT ACCCTTTGGG ACACTTCCGC TTCGCGCCCT
         . . . . . . . . . . . . . . . . . . . . . . . . . . .

+1 uThrLysAla CysLysLysAsp AlaCysPro IleAsnGly GlyTrpGlyP
         ---------- ------------ --------- --------- ----------
    1551 GACCAAAGCC TGCAAGAAAG ACGCCTGCCC CATCAATGGA GGCTGGGGTC
         CTGGTTTCGG ACGTTCTTTC TGCGGACGGG GTAGTTACCT CCGACCCCAG
         . . . . . . . . . . . . . . . . . . . . . . . . . . .

+1 roTrpSerPro TrpAspIle CysSerValThr CysGlyGly GlyValGln
         ----------- --------- ------------ --------- ---------
    1601 CTTGGTCACC ATGGGACATC TGTTCTGTCA CCTGTGGAGG AGGGGTACAG
         GAACCAGTGG TACCCTGTAG ACAAGACAGT GGACACCTCC TCCCCATGTC
         . . . . . . . . . . . . . . . . . . . . . . . . . . .

+1 LysArgSerArg LeuCysAsn AsnProAla ProGlnPheGly GlyLysAs
         ------------ --------- --------- ------------ --------
    1651 AAACGTAGTC GTCTCTGCAA CAACCCCGCA CCCCAGTTTG GAGGCAAGGA
         TTTGCATCAG CAGAGACGTT GTTGGGGCGT GGGGTCAAAC CTCCGTTCCT
```

FIGURE 1E

```
       +1  pCysValGly AspValThrGlu AsnGlnIle CysAsnLys GlnAspCysP
      701  CTGCGTTGGT GATGTAACAG AAAACCAGAT CTGCAACAAG CAGGACTGTC
           GACGCAACCA CTACATTGTC TTTTGGTCTA GACGTTGTTC GTCCTGACAG

+1  roIleAspGly CysLeuSer AsnProCysPhe AlaGlyVal LysCysThr
     1751  CAATTGATGG ATGCCTGTCC AATCCCTGCT TTGCCGGCGT GAAGTGTACT
           GTTAACTACC TACGGACAGG TTAGGGACGA AACGGCCGCA CTTCACATGA

+1  SerTyrProAsp GlySerTrp LysCysGly AlaCysProPro GlyTyrSe
     1801  AGCTACCCTG ATGGCAGCTG GAAATGTGGT GCTTGTCCCC CTGGTTACAG
           TCGATGGGAC TACCGTCGAC CTTTACACCA CGAACAGGGG GACCAATGTC

+1  rGlyAsnGly IleGlnCysThr AspValAsp GluCysLys GluValProA
     1851  TGGAAATGGC ATCCAGTGCA CAGATGTTGA TGAGTGCAAA GAAGTGCCTG
           ACCTTTACCG TAGGTCACGT GTCTACAACT ACTCACGTTT CTTCACGGAC

+1  spAlaCysPhe AsnHisAsn GlyGluHisArg CysGluAsn ThrAspPro
     1901  ATGCCTGCTT CAACCACAAT GGAGAGCACC GGTGTGAGAA CACGGACCCC
           TACGGACGAA GTTGGTGTTA CCTCTCGTGG CCACACTCTT GTGCCTGGGG

+1  GlyTyrAsnCys LeuProCys ProProArg PheThrGlySer GlnProPh
     1951  GGCTACAACT GCCTGCCCTG CCCCCCACGC TTCACCGGCT CACAGCCCTT
           CCGATGTTGA CGGACGGGAC GGGGGGTGCG AAGTGGCCGA GTGTCGGGAA

+1  eGlyGlnGly ValGluHisAla ThrAlaAsn LysGlnVal CysLysProA
     2001  CGGCCAGGGT GTCGAACATG CCACGGCCAA CAAACAGGTG TGCAAGCCCC
           GCCGGTCCCA CAGCTTGTAC GGTGCCGGTT GTTTGTCCAC ACGTTCGGGG

+1  rgAsnProCys ThrAspGly ThrHisAspCys AsnLysAsn AlaLysCys
     2051  GTAACCCCTG CACGGATGGG ACCCACGACT GCAACAAGAA CGCCAAGTGC
           CATTGGGGAC GTGCCTACCC TGGGTGCTGA CGTTGTTCTT GCGGTTCACG

+1  AsnTyrLeuGly HisTyrSer AspProMet TyrArgCysGlu CysLysPr
     2101  AACTACCTGG GCCACTATAG CGACCCCATG TACCGCTGCG AGTGCAAGCC
           TTGATGGACC CGGTGATATC GCTGGGGTAC ATGGCGACGC TCACGTTCGG

+1  oGlyTyrAla GlyAsnGlyIle IleCysGly GluAspThr AspLeuAspG
     2151  TGGCTACGCT GGCAATGGCA TCATCTGCGG GGAGGACACA GACCTGGATG
           ACCGATGCGA CCGTTACCGT AGTAGACGCC CCTCCTGTGT CTGGACCTAC

+1  lyTrpProAsn GluAsnLeu ValCysValAla AsnAlaThr TyrHisCys
     2201  GCTGGCCCAA TGAGAACCTG GTGTGCGTGG CCAATGCGAC TTACCACTGC
           CGACCGGGTT ACTCTTGGAC CACACGCACC GGTTACGCTG AATGGTGACG

+1  LysLysAspAsn CysProAsn LeuProAsn SerGlyGlnGlu AspTyrAs
     2251  AAAAAGGATA ATTGCCCCAA CCTTCCCAAC TCAGGGCAGG AAGACTATGA
           TTTTTCCTAT TAACGGGGTT GGAAGGGTTG AGTCCCGTCC TTCTGATACT
```

FIGURE 1F

```
     +1  pLysAspGly IleGlyAspAla CysAspAsp  AspAspAsp  AsnAspLysI
         ------------------------------------------------------------
    2301 CAAGGATGGA ATTGGTGATG CCTGTGATGA TGACGATGAC AATGATAAAA
         GTTCCTACCT TAACCACTAC GGACACTACT ACTGCTACTG TTACTATTTT
         . . . . . . . . . . . . . . . . . . . . . . . . . . . . . .

+1  leProAspAsp ArgAspAsn CysProPheHis TyrAsnPro AlaGlnTyr
         ------------------------------------------------------------
    2351 TTCCAGATGA CAGGGACAAC TGTCCATTCC ATTACAACCC AGCTCAGTAT
         AAGGTCTACT GTCCCTGTTG ACAGGTAAGG TAATGTTGGG TCGAGTCATA
         . . . . . . . . . . . . . . . . . . . . . . . . . . . . . .

+1  AspTyrAspArg AspAspVal GlyAspArg CysAspAsnCys ProTyrAs
         ------------------------------------------------------------
    2401 GACTATGACA GAGATGATGT GGGAGACCGC TGTGACAACT GTCCCTACAA
         CTGATACTGT CTCTACTACA CCCTCTGGCG ACACTGTTGA CAGGGATGTT
         . . . . . . . . . . . . . . . . . . . . . . . . . . . . . .

+1  nHisAsnPro AspGlnAlaAsp ThrAspAsn AsnGlyGlu GlyAspAlaC
         ------------------------------------------------------------
    2451 CCACAACCCA GATCAGGCAG ACACAGACAA CAATGGGGAA GGAGACGCCT
         GGTGTTGGGT CTAGTCCGTC TGTGTCTGTT GTTACCCCTT CCTCTGCGGA
         . . . . . . . . . . . . . . . . . . . . . . . . . . . . . .

+1  ysAlaAlaAsp IleAspGly AspGlyIleLeu AsnGluArg AspAsnCys
                 PstI
                 ----
    2501 GTGCTGCAGA CATTGATGGA GACGGTATCC TCAATGAACG GGACAACTGC
         CACGACGTCT GTAACTACCT CTGCCATAGG AGTTACTTGC CCTGTTGACG
         . . . . . . . . . . . . . . . . . . . . . . . . . . . . . .

+1  GlnTyrValTyr AsnValAsp GlnArgAsp ThrAspMetAsp GlyValGl
         ------------------------------------------------------------
    2551 CAGTACGTCT ACAATGTGGA CCAGAGAGAC ACTGATATGG ATGGGGTTGG
         GTCATGCAGA TGTTACACCT GGTCTCTCTG TGACTATACC TACCCCAACC
         . . . . . . . . . . . . . . . . . . . . . . . . . . . . . .

+1  yAspGlnCys AspAsnCysPro LeuGluHis AsnProAsp GlnLeuAspS
         ------------------------------------------------------------
    2601 AGATCAGTGT GACAATTGCC CCTTGGAACA CAATCCGGAT CAGCTGGACT
         TCTAGTCACA CTGTTAACGG GGAACCTTGT GTTAGGCCTA GTCGACCTGA
         . . . . . . . . . . . . . . . . . . . . . . . . . . . . . .

+1  erAspSerAsp ArgIleGly AspThrCysAsp AsnAsnGln AspIleAsp
         ------------------------------------------------------------
    2651 CTGACTCAGA CCGGCATTGGA GATACCTGTG ACAACAATCA GGATATTGAT
         GACTGAGTCT GGCGTAACCT CTATGGACAC TGTTGTTAGT CCTATAACTA
         . . . . . . . . . . . . . . . . . . . . . . . . . . . . . .

+1  GluAspGlyHis GlnAsnAsn LeuAspAsn CysProTyrVal ProAsnAl
         ------------------------------------------------------------
    2701 GAAGATGGCC ACCAGAACAA TCTGGACAAC TGTCCCTATG TGCCCAATGC
         CTTCTACCGG TGGTCTTGTT AGACCTGTTG ACAGGGATAC ACGGGTTACG
         . . . . . . . . . . . . . . . . . . . . . . . . . . . . . .

+1  aAsnGlnAla AspHisAspLys AspGlyLys GlyAspAla CysAspHisA
         ------------------------------------------------------------
    2751 CAACCAGGCT GACCATGACA AAGATGGCAA GGGAGATGCC TGTGACCACG
         GTTGGTCCGA CTGGTACTGT TTCTACCGTT CCCTCTACGG ACACTGGTGC
         . . . . . . . . . . . . . . . . . . . . . . . . . . . . . .

+1  spAspAspAsn AspGlyIle ProAspAspLys AspAsnCys ArgLeuVal
                                                           PstI
                                                           ----
    2801 ATGATGACAA CGATGGCATT CCTGATGACA AGGACAACTG CAGACTCGTG
         TACTACTGTT GCTACCGTAA GGACTACTGT TCCTGTTGAC GTCTGAGCAC
```

FIGURE 1G

```
      +1  ProAsnProAsp GlnLysAsp SerAspGly AspGlyArgGly AspAlaCy
          ----------------------------------------------------
2851      CCCAATCCCG ACCAGAAGGA CTCTGACGGC GATGGTCGAG GTGATGCCTG
          GGGTTAGGGC TGGTCTTCCT GAGACTGCCG CTACCAGCTC CACTACGGAC
          . . . . . . . . . . . . . . . . . . . . . . . . . . .

+1  sLysAspAsp PheAspHisAsp SerValPro AspIleAsp AspIleCysP
          ----------------------------------------------------
                                                    ClaI
                                                    ----
2901      CAAAGATGAT TTTGACCATG ACAGTGTGCC AGACATCGAT GACATCTGTC
          GTTTCTACTA AAACTGGTAC TGTCACACGG TCTGTAGCTA CTGTAGACAG
          . . . . . . . . . . . . . . . . . . . . . . . . . . .

+1  roGluAsnVal AspIleSer GluThrAspPhe ArgArgPhe GlnMetIle
          ----------------------------------------------------
2951      CTGAGAATGT TGACATCAGT GAGACCGATT TCCGCCGATT CCAGATGATT
          GACTCTTACA ACTGTAGTCA CTCTGGCTAA AGGCGGCTAA GGTCTACTAA
          . . . . . . . . . . . . . . . . . . . . . . . . . . .

+1  ProLeuAspPro LysGlyThr SerGlnAsn AspProAsnTrp ValValAr
          ----------------------------------------------------
3001      CCTCTGGACC CCAAAGGGAC ATCCCAAAAT GACCCTAACT GGGTTGTACG
          GGAGACCTGG GGTTTCCCTG TAGGGTTTTA CTGGGATTGA CCCAACATGC
          . . . . . . . . . . . . . . . . . . . . . . . . . . .

+1  gHisGlnGly LysGluLeuVal GlnThrVal AsnCysAsp ProGlyLeuA
          ----------------------------------------------------
3051      CCATCAGGGT AAAGAACTCG TCCAGACTGT CAACTGTGAT CCTGGACTCG
          GGTAGTCCCA TTTCTTGAGC AGGTCTGACA GTTGACACTA GGACCTGAGC
          . . . . . . . . . . . . . . . . . . . . . . . . . . .

+1  laValGlyTyr AspGluPhe AsnAlaValAsp PheSerGly ThrPhePhe
          ----------------------------------------------------
3101      CTGTAGGTTA TGATGAGTTT AATGCTGTGG ACTTCAGTGG CACCTTCTTC
          GACATCCAAT ACTACTCAAA TTACGACACC TGAAGTCACC GTGGAAGAAG
          . . . . . . . . . . . . . . . . . . . . . . . . . . .

+1  IleAsnThrGlu ArgAspAsp AspTyrAla GlyPheValPhe GlyTyrGl
          ----------------------------------------------------
3151      ATCAACACCG AAAGGGACGA TGACTATGCT GGATTTGTCT TTGGCTACCA
          TAGTTGTGGC TTTCCCTGCT ACTGATACGA CCTAAACAGA AACCGATGGT
          . . . . . . . . . . . . . . . . . . . . . . . . . . .

+1  nSerSerSer ArgPheTyrVal ValMetTrp LysGlnVal ThrGlnSerT
          ----------------------------------------------------
3201      GTCCAGCAGC CGCTTTTATG TTGTGATGTG GAAGCAAGTC ACCCAGTCCT
          CAGGTCGTCG GCGAAAATAC AACACTACAC CTTCGTTCAG TGGGTCAGGA
          . . . . . . . . . . . . . . . . . . . . . . . . . . .

+1  yrTrpAspThr AsnProThr ArgAlaGlnGly TyrSerGly LeuSerVal
          ----------------------------------------------------
3251      ACTGGGACAC CAACCCCACG AGGGCTCAGG GATACTCGGG CCTTTCTGTG
          TGACCCTGTG GTTGGGGTGC TCCCGAGTCC CTATGAGCCC GGAAAGACAC
          . . . . . . . . . . . . . . . . . . . . . . . . . . .

+1  LysValValAsn SerThrThr GlyProGly GluHisLeuArg AsnAlaLe
          ----------------------------------------------------
3301      AAAGTTGTAA ACTCCACCAC AGGGCCTGGC GAGCACCTGC GGAACGCCCT
          TTTCAACATT TGAGGTGGTG TCCCGGACCG CTCGTGGACG CCTTGCGGGA
          . . . . . . . . . . . . . . . . . . . . . . . . . . .

+1  uTrpHisThr GlyAsnThrPro GlyGlnVal ArgThrLeu TrpHisAspP
          ----------------------------------------------------
3351      GTGGCACACA GGAAACACCC CTGGCCAGGT GCGCACCCTG TGGCATGACC
          CACCGTGTGT CCTTTGTGGG GACCGGTCCA CGCGTGGGAC ACCGTACTGG
```

FIGURE 1H

```
      +1 roArgHisIle GlyTrpLys AspPheThrAla TyrArgTrp ArgLeuSer
         ----------------------------------------------------------
3401     CTCGTCACAT AGGCTGGAAA GATTTCACCG CCTACAGATG GCGTCTCAGC
         GAGCAGTGTA TCCGACCTTT CTAAAGTGGC GGATGTCTAC CGCAGAGTCG
    . . . . . . . . . . . . . . . . . . . . . . . . . . . . . . . .
      +1 HisArgProLys ThrGlyPhe IleArgVal ValMetTyrGlu GlyLysLy
         ----------------------------------------------------------
3451     CACAGGCCAA AGACGGGTTT CATTAGAGTG GTGATGTATG AAGGGAAGAA
         GTGTCCGGTT TCTGCCCAAA GTAATCTCAC CACTACATAC TTCCCTTCTT
    . . . . . . . . . . . . . . . . . . . . . . . . . . . . . . . .
      +1 sIleMetAla AspSerGlyPro IleTyrAsp LysThrTyr AlaGlyGlyA
         ----------------------------------------------------------
3501     AATCATGGCT GACTCAGGAC CCATCTATGA TAAAACCTAT GCTGGTGGTA
         TTAGTACCGA CTGAGTCCTG GGTAGATACT ATTTTGGATA CGACCACCAT
    . . . . . . . . . . . . . . . . . . . . . . . . . . . . . . . .
      +1 rgLeuGlyLeu PheValPhe SerGlnGluMet ValPhePhe SerAspLeu
         ----------------------------------------------------------
3551     GACTAGGGTT GTTTGTCTTC TCTCAAGAAA TGGTGTTCTT CTCTGACCTG
         CTGATCCCAA CAAACAGAAG AGAGTTCTTT ACCACAAGAA GAGACTGGAC
    . . . . . . . . . . . . . . . . . . . . . . . . . . . . . . . .
      +1 LysTyrGluCys ArgAspPro
         ---------------------->
3601     AAATACGAAT GTAGAGATCC CTAATCATCA AATTGTTGAT TGAAAGACTG
         TTTATGCTTA CATCTCTAGG GATTAGTAGT TTAACAACTA ACTTTCTGAC
    . . . . . . . . . . . . . . . . . . . . . . . . . . . . . . . .
3651     ATCATAAACC AATGCTGGTA TTGCACCTTC TGGAACTATG GCTTGAGAA
         TAGTATTTGG TTACGACCAT AACGTGGAAG ACCTTGATAC CCGAACTCTT
    . . . . . . . . . . . . . . . . . . . . . . . . . . . . . . . .
3701     AACCCCCAGG ATCACTTCTC CTTGGCTTCC TTCTTTTCTG TGCTTGCATC
         TTGGGGGTCC TAGTGAAGAG GAACCGAAGG AAGAAAAGAC ACGAACGTAG
    . . . . . . . . . . . . . . . . . . . . . . . . . . . . . . . .
3751     AGTGTGGACT CCTAGAACGT GCGACCTGCC TCAAGAAAAT GCAGTTTTCA
         TCACACCTGA GGATCTTGCA CGCTGGACGG AGTTCTTTTA CGTCAAAAGT
    . . . . . . . . . . . . . . . . . . . . . . . . . . . . . . . .
3801     AAAACAGACT CATCAGCATT CAGCCTCCAA TGAATAAGAC ATCTTCCAAG
         TTTTGTCTGA GTAGTCGTAA GTCGGAGGTT ACTTATTCTG TAGAAGGTTC
    . . . . . . . . . . . . . . . . . . . . . . . . . . . . . . . .
3851     CATATAAACA ATTGCTTTGG TTTCCTTTTG AAAAAGCATC TACTTGCTTC
         GTATATTTGT TAACGAAACC AAAGGAAAAC TTTTTCGTAG ATGAACGAAG
    . . . . . . . . . . . . . . . . . . . . . . . . . . . . . . . .
3901     AGTTGGGAAG GTGCCCATTC CACTCTGCCT TTGTCACAGA GCAGGGTGCT
         TCAACCCTTC CACGGGTAAG GTGAGACGGA AACAGTGTCT CGTCCCACGA
    . . . . . . . . . . . . . . . . . . . . . . . . . . . . . . . .
3951     ATTGTGAGGC CATCTCTGAG CAGTGGACTC AAAAGCATTT TCAGGCATGT
         TAACACTCCG GTAGAGACTC GTCACCTGAG TTTTCGTAAA AGTCCGTACA
    . . . . . . . . . . . . . . . . . . . . . . . . . . . . . . . .
4001     CAGAGAAGGG AGGACTCACT AGAATTAGCA AACAAAACCA CCCTGACATC
         GTCTCTTCCC TCCTGAGTGA TCTTAATCGT TTGTTTTGGT GGGACTGTAG
    . . . . . . . . . . . . . . . . . . . . . . . . . . . . . . . .
4051     CTCCTTCAGG AACACGGGGA GCAGAGGCCA AAGCACTAAG GGGAGGGCGC
         GAGGAAGTCC TTGTGCCCCT CGTCTCCGGT TTCGTGATTC CCCTCCCGCG
    . . . . . . . . . . . . . . . . . . . . . . . . . . . . . . . .
4101     ATACCCGAGA CGATTGTATG AAGAAAATAT GGAGGAACTG TTACATGTTC
         TATGGGCTCT GCTAACATAC TTCTTTTATA CCTCCTTGAC AATGTACAAG
    . . . . . . . . . . . . . . . . . . . . . . . . . . . . . . . .
4151     GGTACTAAGT CATTTTCAGG GGATTGAAAG ACTATTCCTG GATTTCATGA
         CCATGATTCA GTAAAAGTCC CCTAACTTTC TGATAACGAC CTAAAGTACT
```

FIGURE 1I

```
4201  TGCTGACTGG CGTTAGCTGA TTAACCCATG TAAATAGGCA CTTAAATAGA
      ACGACTGACC GCAATCGACT AATTGGGTAC ATTTATCCGT GAATTTATCT

4251  AGCAGGAAAG GGAGACAAAG ACTGGCTTCT GGACTTCCTC CCTGATCCCC
      TCGTCCTTTC CCTCTGTTTC TGACCGAAGA CCTGAAGGAG GGACTAGGGG

4301  ACCCTTACTC ATCACCTTGC AGTGGCCAGA ATTAGGGAAT CAGAATCAAA
      TGGGAATGAG TAGTGGAACG TCACCGGTCT TAATCCCTTA GTCTTAGTTT

4351  CCAGTGTAAG GCAGTGCTGG CTGCCATTGC CTGGTCACAT TGAAATTGGT
      GGTCACATTC CGTCACGACC GACGGTAACG GACCAGTGTA ACTTTAACCA
                XbaI
4401  GGCTTCATTC TAGATGTAGC TTGTGCAGAT GTAGCAGGAA AATAGGAAAA
      CCGAAGTAAG ATCTACATCG AACACGTCTA CATCGTCCTT TTATCCTTTT

4451  CCTACCATCT CAGTGAGCAC CAGCTGCCTC CCAAAGGAGG GGCAGCCGTG
      GGATGGTAGA GTCACTCGTG GTCGACGGAG GGTTTCCTCC CCGTCGGCAC

4501  CTTATATTTT TATGGTTACA ATGGCACAAA ATTATTATCA ACCTAACTAA
      GAATATAAAA ATACCAATGT TACCGTGTTT TAATAATAGT TGGATTGATT

4551  AACATTCCTT TTCTCTTTTT TCCGTAATTA CTAGGTAGTT TTCTAATTCT
      TTGTAAGGAA AAGAGAAAAA AGGCATTAAT GATCCATCAA AAGATTAAGA
                                                  SspI
4601  CTCTTTTGGA AGTATGATTT TTTTAAAGTC TTTACGATGT AAAATATTTA
      GAGAAAACCT TCATACTAAA AAAATTTCAG AAATGCTACA TTTTATAAAT

4651  TTTTTTACTT ATTCTGGAAG ATCTGGCTGA AGGATTATTC ATGGAACAGG
      AAAAAATGAA TAAGACCTTC TAGACCGACT TCCTAATAAG TACCTTGTCC

4701  AAGAAGCGTA AAGACTATCC ATGTCATCTT TGTTGAGAGT CTTCGTGACT
      TTCTTCGCAT TTCTGATAGG TACAGTAGAA ACAACTCTCA GAAGCACTGA

4751  GTAAGATTGT AAATACAGAT TATTTATTAA CTCTGTTCTG CCTGGAAATT
      CATTCTAACA TTTATGTCTA ATAAATAATT GAGACAAGAC GGACCTTTAA

4801  TAGGCTTCAT ACGGAAAGTG TTTGAGAGCA AGTAGTTGAC ATTTATCAGC
      ATCCGAAGTA TGCCTTTCAC AAACTCTCGT TCATCAACTG TAAATAGTCG

4851  AAATCTCTTG CAAGAACAGC ACAAGGAAAA TCAGTCTAAT AAGCTGCTCT
      TTTAGAGAAC GTTCTTGTCG TGTTCCTTTT AGTCAGATTA TTCGACGAGA

4901  GCCCCTTGTG CTCAGAGTGG ATGTTATGGG ATTCCTTTTT TCTCTGTTTT
      CGGGGAACAC GAGTCTCACC TACAATACCC TAAGGAAAAA AGAGACAAAA

4951  ATCTTTTCAA GTGGAATTAG TTGGTTATCC ATTTGCAAAT GTTTAAATT
      TAGAAAAGTT CACCTTAATC AACCAATAGG TAAACGTTTA CAAAATTTAA

5001  GCAAAGAAAG CCATGAGGTC TTCAATACTG TTTTACCCCA TCCCTTGTGC
      CGTTTCTTTC GGTACTCCAG AAGTTATGAC AAAATGGGGT AGGGAACACG

5051  ATATTTCCAG GGAGAAGGAA AGCATATACA CTTTTTTCTT TCATTTTTCC
      TATAAAGGTC CCTCTTCCTT TCGTATATGT GAAAAAAGAA AGTAAAAAGG
```

FIGURE 1J

```
                                                        SspI
                                                       ─────
5101  AAAAGAGAAA AAAATGACAA AAGGTGAAAC TTACATACAA ATATTACCTC
      TTTTCTCTTT TTTTACTGTT TTCCACTTTG AATGTATGTT TATAATGGAG

5151  ATTTGTTGTG TGACTGAGTA AAGAATTTTT GGATCAAGCG GAAAGAGTTT
      TAAACAACAC ACTGACTCAT TTCTTAAAAA CCTAGTTCGC CTTTCTCAAA

5201  AAGTGTCTAA CAAACTTAAA GCTACTGTAG TACCTAAAAA GTCAGTGTTG
      TTCACAGATT GTTTGAATTT CGATGACATC ATGGATTTTT CAGTCACAAC

PstI
            ─────
5251  TACATAGCAT AAAAACTCTG CAGAGAAGTA TTCCCAATAA GGAAATAGCA
      ATGTATCGTA TTTTTGAGAC GTCTCTTCAT AAGGGTTATT CCTTTATCGT

5301  TTGAAATGTT AAATACAATT TCTGAAAGTT ATGTTTTTTT TCTATCATCT
      AACTTTACAA TTTATGTTAA AGACTTTCAA TACAAAAAAA AGATAGTAGA

5351  GGTATACCAT TGCTTTATTT TTATAAATTA TTTTCTCATT GCCATTGGAA
      CCATATGGTA ACGAAATAAA AATATTTAAT AAAAGAGTAA CGGTAACCTT

SspI
       ─────
5401  TAGAATATTC AGATTGTGTA GATATGCTAT TTAAATAATT TATCAGGAAA
      ATCTTATAAG TCTAACACAT CTATACGATA AATTTATTAA ATAGTCCTTT

5451  TACTGCCTGT AGAGTTAGTA TTTCTATTTT TATATAATGT TTGCACACTG
      ATGACGGACA TCTCAATCAT AAAGATAAAA ATATATTACA AACGTGTGAC

5501  AATTGAAGAA TTGTTGGTTT TTTCTTTTTT TTGTTTTTTT TTTTTTTTTT
      TTAACTTCTT AACAACCAAA AAAGAAAAAA AACAAAAAAA AAAAAAAAAA

5551  TTTTTTTTTG CTTTTGACCT CCCATTTTTA CTATTTGCCA ATACCTTTTT
      AAAAAAAAAC GAAAACTGGA GGGTAAAAAT GATAAACGGT TATGGAAAAA

5601  CTAGGAATGT GCTTTTTTTT GTACACATTT TTATCCATTT TACATTCTAA
      GATCCTTACA CGAAAAAAAA CATGTGTAAA AATAGGTAAA ATGTAAGATT

5651  AGCAGTGTAA GTTGTATATT ACTGTTTCTT ATGTACAAGG AACAACAATA
      TCGTCACATT CAACATATAA TGACAAAGAA TACATGTTCC TTGTTGTTAT

5701  AATCATATGG AAATTTATAT TT
      TTAGTATACC TTTAAATATA AA
```

FIGURE 1K

```
   1  MGLAWGLGVL FLMHVCGTNR IPESGGDNSV FDIFELTGAA RKGSGRRLVK
  51  GPDPSSPAFR IEDANLIPPV PDDKFQDLVD AVRAEKGFLL LASLRQMKKT
 101  RGTLLALERK DHSGQVFSVV SNGKAGTLDL SLTVQGKQHV VSVEEALLAT
 151  GQWKSITLFV QEDRAQLYID CEKMENAELD VPIQSVFTRD LASIARLRIA
 201  KGGVNDNFQG VLQNVRFVFG TTPEDILRNK GCSSSTSVLL TLDNNVVNGS
 251  SPAIRTNYIG HKTKDLQAIC GISCDELSSM VLELRGLRTI VTTLQDSIRK
 301  VTEENKELAN ELRRPPLCYH NGVQYRNNEE WTVDSCTECH CQNSVTICKK
 351  VSCPIMPCSN ATVPDGECCP RCWPSDSADD GWSPWSEWTS CSTSCGNGIQ
 401  QRGRSCDSLN NRCEGSSVQT RTCHIQECDK RFKQDGGWSH WSPWSSCSVT
 451  CGDGVITRIR LCNSPSPQMN GKPCEGEARE TKACKKDACP INGGWGPWSP
 501  WDICSVTCGG GVQKRSRLCN NPAPQFGGKD CVGDVTENQI CNKQDCPIDG
 551  CLSNPCFAGV KCTSYPDGSW KCGACPPGYS GNGIQCTDVD ECKEVPDACF
 601  NHNGEHRCEN TDPGYNCLPC PPRFTGSQPF GQGVEHATAN KQVCKPRNPC
 651  TDGTHDCNKN AKCNYLGHYS DPMYRCECKP GYAGNGIICG EDTDLDGWPN
 701  ENLVCVANAT YHCKKDNCPN LPNSGQEDYD KDGIGDACDD DDDNDKIPDD
 751  RDNCPFHYNP AQYDYDRDDV GDRCDNCPYN HNPDQADTDN NGEGDACAAD
 801  IDGDGILNER DNCQYVYNVD QRDTDMDGVG DQCDNCPLEH NPDQLDSDSD
 851  RIGDTCDNNQ DIDEDGHQNN LDNCPYVPNA NQADHDKDGK GDACDHDDDN
 901  DGIPDDKDNC RLVPNPDQKD SDGDGRGDAC KDDFDHDSVP DIDDICPENV
 951  DISETDFRRF QMIPLDPKGT SQNDPNWVVR HQGKELVQTV NCDPGLAVGY
1001  DEFNAVDFSG TFFINTERDD DYAGFVFGYQ SSSRFYVVMW KQVTQSYWDT
1051  NPTRAQGYSG LSVKVVNSTT GPGEHLRNAL WHTGNTPGQV RTLWHDPRHI
1101  GWKDFTAYRW RLSHRPKTGF IRVVMYEGKK IMADSGPIYD KTYAGGRLGL
1151  FVFSQEMVFF SDLKYECRDP
```

FIGURE 2B

```
                                                               Asp718
                                                               ~~~~
  1  AGCATCTGAT GCACAAAATA GAGTGGTGGT TGCTTCTTTC CACACAGGTA
     TCGTAGACTA CGTGTTTTAT CTCACCACCA ACGAAGAAAG CTGTGTCCAT
     AlaAspSerAla CysPheLeu ThrThrThr AlaGluLysTrp ValProVa

Asp718
     ~~
 51  CCCCATAATA GACTGTGACC CACAATTTTT CGCTCCCTCC TCCACAGGTG
     GGGGTATTAT CTGACACTGG GTGTTAAAAA GCGAGGGAGG AGGTGTCCAC
     GlyTyrTyr  ValThrValTrp LeuLysGlu SerGlyGly GlyCysThrV
                   gp120 fusion ◀——┤         Domain #2

BamHI
                  ~~~~~~~
101  ACAGAACAGT TGCAGAGCCG GATCCTTGTG ATCACACCAT CACCACATGT
     TGTCTTGTCA ACGTCTCGGC CTAGGAACAC TAGTGTGGTA GTGGTGTACA
     alSerCysAsn CysLeuArg IleArgThrIle ValGlyAsp GlyCysThr
                                                  Domain #1

151  CACAGAACAA GAAGACCCCT TGCGGGCGGC CCCGGTGAGT TCAAAGATGT
     GTGTCTTGTT CTTCTGGGGA ACGCCCGCCG GGGCCACTCA AGTTTCTACA
     ValSerCysSer SerGlyLys ArgAlaAla GlyThrLeuGlu PheIleAs

201  CAAACACGCT GTTGTCTCCG CCAGACTCTG GAATGCGGTT GGTGCCACAC
     GTTTGTGCGA CAACAGAGGC GGTCTGAGAC CTTACGCCAA CCACGGTGTG
     pPheValSer AsnAspGlyGly SerGluPro IleArgAsn ThrGlyCysV

PstI
                                                  ~~~~~~
251  ACATGCATCA GGAACAGGAC GCCTAGTCCC CAGGCCAGCC CCATCTGCAG
     TGTACGTAGT CCTTGTCCTG CGGATCAGGG GTCCGGTCGG GGTAGACGTC
     alHisMetLeu PheLeuVal GlyLeuGlyTrp AlaLeuGly Met  (SEQ ID NO.: 10)
                                               ◀—— Translation Start 301  AAAAGACCCA TGGAAAGGAA CAGTCTGTTA GTCTGTCAGC TATTATGTCT  ⎫
     TTTTCTGGGT ACCTTTCCTT GTCAGACAAT CAGACAGTCG ATAATACAGA  ⎪

351  GGTGGCGCGC GCGGCAGCAA CGAGTACTGC TCAGACTACA CTGCCCTCCA  ⎪
     CCACCGCGCG CGCCGTCGTT GCTCATGACG AGTCTGATGT GACGGGAGGT  ⎬ CMV IE
                                                            ⎪ Promotor
401  CCGTTAACAG CACCGCAACG GGAGTTACCT CTGACTCTTA TCAGAATACA  ⎪
     GGCAATTGTC GTGGCGTTGC CCTCAATGGA GACTGAGAAT AGTCTTATGT  ⎪

451  ACAACTCAAG CTGCCTGCAT CTTCTTCTGC CGCTGCCTTA AGTCTTCCAT  ⎪
     TGTTGAGTTC GACGGACGTA GAAGAAGACG GCGACGGAAT TCAGAAGGTA  ⎭

501  CTGCGTCAGC CGTGCGAGCC CAATCTTCAC GCTCATTTTC AGACACATAC
     GACGCAGTCG GCACGCTCGG GTTAGAAGTG CGAGTAAAAG TCTGTCTATG

551  CCTACCG    (SEQ ID NO.: 8)
     GGATGGC    (SEQ ID NO.: 9)
```

ENHANCEMENT OF THE IMMUNE RESPONSE USING CD36-BINDING DOMAIN

RELATED APPLICATIONS

This application claims priority to U.S. Ser. No. 60/341,771 filed Dec. 12, 2001, which is hereby incorporated by reference.

FIELD OF THE INVENTION

The invention relates to reagents and methods for enhancing an immune response using CD36 binding region/antigen hybrid polypeptides or polynucleotides encoding the hybrid polypeptides.

BACKGROUND

Cells undergoing programmed cell death (i.e. apoptosis) are recognized by phagocytes such as macrophages and immature dendritic cells (Albert, M. L., et al., "Immature dendritic cells phagocytose apoptotic cells via alpha v beta 5 and CD36, and cross-present antigens to cytotoxic T lymphocytes," *J. Exp. Med.* 188(7):1359 (1998)). This recognition leads to the uptake and degradation of the dying cells.

Some of the molecular details of this recognition are now known. For example, recognition of and adherence to apoptotic cells by phagocytes occurs by several mechanisms including a CD36-dependent mechanism (Albert, M. L., et al., (1998)). CD36 is a cell surface glycoprotein that is expressed on dendritic cells, monocytes, and macrophages (Platt, N., et al., *Proc. Natl. Acad. Sci.*, 93: 12456 (1996)). Furthermore, CD36 is a receptor for thrombospondin. (Asch et al. "Isolation of the thrombospondin membrane receptor," *J. Clin. Invest.*, 79:1054 (1987)).

Thrombospondins are a family of extracellular matrix adhesive proteins. Thrombospondin 1 (TSP 1) inhibits angiogenesis and modulates endothelial cell motility, adhesion, and cell growth. Thrombospondin 1 has multiple functional domains, including a type I repeat which has homology with properdin (Arch, A. S., et al., *Biochem. Biophys. Res. Commun.,* 182(3):1208 (1992); Crombie, R., et al., *J. Exp. Med.,* 187(1): 25 (1998); Magnetto, S., et al., *Cell Biochem. Funct,* 16(3): 211 (1998); Carron, J. A., et al., *Biochem. Biophys. Res. Commun.* 270(3): 1124 (2000); and Li, W., et al., *J. Biol. Chem.,* 268:16179 (1993)). Within the type I repeat are two CSVTCG (SEQ ID NO.: 11) sequences that serve as binding sites for CD36. (Pearce, S. F. A., et al., "Recombinant GST/CD36 fusion proteins define a thrombospondin binding domain: evidence for a single calcium-dependent binding site on CD36," *J. Biol. Chem.* 270: 2981 (1995); and Asch, A. S., et al., "Thrombospondin sequence motif (CSVTCG; SEQ ID NO.: 11) is responsible for CD36 binding," *Biochem. Biophys. Res. Commun.* 182: 1208 (1992)).

Engulfment of apoptotic bodies by phagocytes, including dendritic cells, is mediated by CD36 and results in cross-presentation of antigens to cytotoxic T-lymphocytes. (Albert M. L., et al. (1998)). Furthermore, human monocyte-derived macrophages phagocytose apoptotic neutrophils and eosinophils through a thrombospondin/CD36 dependent mechanism. (Stern et al., "Human monocyte-derived macrophage phagocytosis of eosinophils undergoing apoptosis. Mediation by alpha v beta 3/CD36/thrombospondin recognition mechanisms and lack phlogistic response," *Am. J. Pathol.* 149(3):911 (1996)). Therefore, CD36 and thrombospondin play an important role in the recognition and phagocytosis of apoptotic cells.

Classical vaccine technology has included the development of both live and inactivated vaccines. Live vaccines are typically attenuated non-pathogenic versions of an infectious agent that are capable of priming an immune response directed against a pathogenic version of the infectious agent. In recent years there have been advances in the development of live recombinant vaccines (e.g., recombinant poxviruses) in which foreign antigens of interest are expressed from a viral vector. Although there are numerous examples of live vaccines that are very effective (e.g., vaccinia in the eradication of smallpox), there are inherent risks associated with live vectors. For example, it is possible to contaminate live vaccines with harmful adventitious agents, since live vaccines cannot be subjected to harsh inactivation or purification procedures. Additionally, there is a possibility when using live vaccine vectors, of "runaway vaccination" causing systemic viremia in immunocomprised recipients. Finally, live viral vectors elicit strong inflammatory and immunogenic responses against vector components that limit the utility of repeat administration.

Inactivated vaccines are comprised of killed whole pathogens, or soluble proteins or protein subunits. While generally considered safe, the efficacy of inactivated vaccines at eliciting broad, long-lasting responses is of concern for some vaccine preparations. In fact, most inactivated vaccines fail to produce a significant CD8+ cellular response necessary for cytolytic immune activity. Recombinant proteins are promising inactive vaccine or immunogenic composition candidates because they can be produced at high yield and purity. However, recombinant proteins can be poorly immunogenic. Therefore, there is a need for methods and compositions that enhance the immune response to inactivated vaccines, especially vaccines containing recombinant proteins.

Adjuvants have been used for many years to enhance the immune response to antigens present in vaccines, including subunit or component vaccines comprised of recombinant proteins. Currently, alum is the most commonly used adjuvant for human administration. However, although its efficacy has been established, it is ineffective for certain vaccinations (e.g. influenza vaccination) and inconsistently elicits an immune response with certain immunogens. Therefore, there remains a need for safe, effective, and easily manufactured compositions and methods for enhancing an immune response.

Recently, nucleic acid vectored vaccines (NAVAC) have been developed. These vaccines involve direct inoculation of an organism with nucleic acid vectors containing inserts encoding antigens (i.e. genetic vaccination). It appears that both the method (e.g. intramuscular injection, epidermal Gene Gun-mediated administration) and route of inoculation (e.g. intramuscular, epidermal, mucosal) are important in determining the efficacy of the immune response for NAVAC (Robinson et al., *Vaccine* 11:957 (1993); Ulmer et al., *Vaccine* 15:792 (1997); and Shiver et al., *Vaccine,* 15:884 (1997)). This has led to inconsistent stimulation of an immune response using NAVAC. Therefore, there remains a need for effective methods for using NAVAC to consistently elicit a strong immune response.

Despite our increasing understanding of the complex cellular and molecular interactions involved in certain aspects of an immune response, there remains a need for improved methods and compositions, such as vaccines, for enhancing an immune response. More specifically, there remains a need to develop methods and reagents that utilize our growing understanding of antigen presenting cell-recognition molecules, such as CD36, and pathways that depend on these molecules, such as CD36/thrombospondin-dependent pathways.

SUMMARY OF THE INVENTION

The present invention provides improved methods for immunizing a host against an antigen. In one embodiment, an isolated chimeric nucleic acid molecule encoding a chimeric polypeptide is provided. In a preferred embodiment, the chimeric nucleic acid molecule comprises a nucleic acid sequence encoding at least one CD36 binding domain and another nucleic acid sequence encoding at least one immunogenic amino acid sequence (i.e., antigen). Following introduction of the nucleic acid molecule into a host, a chimeric polypeptide is expressed resulting in an immune response against the immunogenic amino acid sequence. Thus, in one embodiment, the present invention provides an isolated nucleic acid molecule encoding an immunogenic chimeric polypeptide, the nucleic acid molecule being suitable for administration to a host, either alone or as a pharmaceutical composition. In another embodiment, the present invention provides an immunogenic chimeric polypeptide suitable for administration to a host, either alone or as a pharmaceutical composition. In yet another embodiment, a method of immunizing a host using the isolated nucleic acid molecule or the chimeric polypeptide is provided.

BRIEF DESCRIPTION OF THE DRAWINGS

FIG. 1 illustrates a restriction map (FIG. 1A), the nucleotide sequence (FIGS. 1B-J; see also GenBank Accession Number X14787) and the amino acid sequence (FIG. 1K) of mature thrombospondin 1 (TSP1). The signal sequence is found at amino acids 1-31 and the connecting peptide at amino acids 32-44; the CD36 binding domains are found at amino acids 504-511 and 447-452; and, the beta sheet region is found at amino acids 453-463.

FIG. 2 illustrates the structure (FIG. 2A) and nucleotide as well as amino acid sequence (FIG. 2B) of the chimera pVITHROMBgp120FU. In FIG. 2B, The N-terminus of the thrombo=gp120 hybrid polypeptide begins at the methionine residue encoded by the codon adjacent to the Pst I site.

FIG. 3 shows V3 CTL activity following a single immunization with control plasmid (open squares), plasmid gp120 (filled diamonds), plasmid thrombo=gp120 (filled triangles) or vP1008 (open squares).

FIG. 4 shows V3 CTL activity three weeks after a second immunization given three weeks after a first immunization, with control plasmid (open squares), plasmid gp120 (filled diamonds), plasmid thrombo=gp120 (filled triangles) or vP1008 (open squares).

FIG. 5 shows anti-gp160 antibody production following immunization during weeks 0 and 3 with plasmid thrombo=gp120. Individual sera from each mouse was diluted 1:400 and assayed by kinetics ELISA (KELISA) using recombinant HIV MN/BRU envelope glycoprotein as antigen.

FIG. 6 shows V3 activity three weeks after a second immunization with control plasmid (open squares), plasmid gp120 (filled diamonds), plasmid thrombo=gp120 (filled triangles) or vP1008 (open squares).

FIG. 7 shows V3 (gp120) CTL activity at seven weeks after a second immunization with control plasmid (open squares), plasmid gp120 (filled diamonds), plasmid thrombo=gp120 (filled triangles) or vP1008 (open squares).

FIG. 8 shows anti-gp160 antibody responses to gp120 following two successive immunizations with control plasmid (vical), plasmid gp120 (vical-gp120), plasmid thrombo=gp120 or vP1008 after a first immunization (week 0) and a second immunization (week 3). KELISA results for three mice from each group are graphed individually (open squares, closed triangles, and closed diamonds). Antibody responses were calculated at the time of immunization, and at 3 weeks, 6 weeks, 8 weeks, and 10 weeks after the first immunization.

DESCRIPTION OF THE PREFERRED EMBODIMENTS

The present invention relates to a chimeric nucleic acid molecule comprising a nucleic acid sequence encoding one or more CD36 binding regions positioned in-frame to one or more nucleic acid sequences encoding one or more immunogenic amino acid sequences (i.e., antigens). Such as nucleic acid molecule is referred to as a chimeric or hybrid nucleic acid. The nucleic acid sequence(s) encoding the one or more CD36 binding region(s) may be positioned upstream (5') or downstream (3') from the nucleic acid sequence(s) encoding the one or more antigens, provided a chimeric polypeptide comprising both the CD36 binding region and antigenic region is expressed in cells transfected with the chimeric nucleic acid molecule. Preferably, the nucleic acid sequence(s) encoding the one or more CD36 binding region(s) is ligated upstream from the nucleic acid(s) encoding the one or more antigens. In preferred embodiments, the chimeric nucleic acid molecule is admixed in a pharmaceutically acceptable carrier to form the immunogenic compositions of the current invention. In other preferred embodiments, the chimeric polypeptide is admixed in a pharmaceutically acceptable carrier to form the immunogenic compositions of the current invention. Recombinant DNA methods used herein are generally those set forth in commonly used references such as Sambrook et al., *Molecular Cloning: A Laboratory Manual* (Cold Spring Harbor Laboratory Press, 1989) and/or *Current Protocols in Molecular Biology* (Ausubel et al., Eds., Green publishers inc. and Wiley and Sons 1994). All references cited in this application are expressly incorporated by reference herein.

The term "CD36 binding region" means a polypeptide sequence capable of binding to the cell surface glycoprotein CD36 in solid-phase binding assays (see, for example, Crombie et al., J. Exp. Med., 187: 25 (1998); and Pearce et al., J. Biol. Chem. 270: 2981 (1995)). Typically, the CD36 binding region includes sequences that do not bind CD36 in the absence of other sequences within the CD36 binding region. The boundaries of the CD36 binding region are typically defined by identifying the amino or carboxy-most polypeptide subsegments within the CD36 binding region that are capable of binding CD36 or enhancing binding to CD36 in solid-phase binding assays. In a preferred embodiment, the CD36 binding region of the present invention has the amino acid sequence of the CD36 binding region of TSP1 (SEQ ID NO.: 7; FIGS. 1B-K; GenBank Accession No. X14787). For the purposes of practicing the present invention, this region preferably comprises amino acids 447-463 ligated with or without intervening amino acids to amino acids 504-511 of TSP1.

Within the CD36 binding region are CD36 binding domains, which are subsegments of the CD36 binding region that independently bind CD36 in solid-phase binding assays. Binding of the CD36 binding region to the cell surface glycoprotein CD36 occurs through one or more of these CD36 binding domains. The CD36 binding domain typically comprises the amino acid sequence CSVTCG (SEQ ID NO.: 11) or sequences related thereto. A sequence related to the sequence CSVTCG (SEQ ID NO.: 11), or "consisting essentially of" CSVTCG (SEQ ID NO.: 11) is a sequence that has at least 4 of the amino amino acids in CSVTCG (SEQ ID NO.: 11), or comprises conservative substitutions of at least 4 of the amino acids in CSVTCG (SEQ ID NO.: 11), and retains the ability to bind CD36 in solid-phase binding assays. Representative CD36 binding domains are found at amino acids 447-452 and amino acids 504-511 of TSP1 (FIGS. 1B-K).

In one embodiment, the CD36 binding region contains at least two CD36 binding domains. The domains are typically separated by spacer regions (or "spacer amino acids") that preferably have a beta sheet conformation. Methods are known in the art for predicting whether a polypeptide region will have a beta sheet conformation based on the primary sequence of the polypeptide. In addition, the conformation of polypeptide regions can be determined experimentally using well-known methods. The beta sheet spacers may be of any length provided that the resultant CD36 binding region enhances an immune response. It is preferred that the spacers are approximately 11 amino acids in length. It is more preferred that the spacer be 11 amino acids in length. In a most preferred embodiment, the spacer is identical to amino acids 453-463 of TSP1 or has the sequence DGVITRIRLCN (FIGS. 1B-K). In a preferred embodiment, the CD36 binding region contains two CD36 binding domains separated by a spacer region of about 11 amino acids.

The nucleic acid sequence(s) encoding the one or more antigens encodes an amino acid sequence that causes an immune response within a host upon expression within the host. It is preferred that, following expression of an effective amount of chimeric nucleic acid or administration of an effective amount the chimeric polypeptide, the host is immunized against the antigen. An "effective amount" is that which enhances an immune response as measured using assays known in the art including, for example, antibody assays, antigen specific cytotoxicity assays, and assays measuring the expression of cytokines. In preferred embodiments, the chimeric nucleic acid molecule or chimeric polypeptide functions as a vaccine. As is understood in the art, a vaccine is an immunogenic composition containing an antigen that, when administered to an animal, stimulates an immune response that at least partially protects the animal from challenge by a cell or organism expressing the antigen. "Partially protects the animal" means that the immunogenic composition elicits an antibody-based or cytotoxic T lymphocyte response against the antigen.

For example, where the antigen is a tumor antigen, the host is preferably protected from the development of a tumor and/or the host acquires the ability to eliminate an existing tumor from the body. The term "tumor antigen" as used herein includes both tumor associated antigens (TAAs) and tumor specific antigens (TSAs), where a cancerous cell is the source of the antigen. A TAA is an antigen that is expressed on the surface of a tumor cell in higher amounts than is observed on normal cells or an antigen that is expressed on normal cells during fetal development. A TSA is an antigen that is unique to tumor cells and is not expressed on normal cells. The term tumor antigen includes TAAs or TSAs, antigenic fragments thereof, and modified versions that retain their antigenicity.

Suitable TAA or TSA may include wild-type or mutated antigens such as, for example, gp100 (Cox et al., *Science*, 264:716-719 (1994)), MART-1/Melan A (Kawakami et al., *J. Exp. Med.*, 180:347-352 (1994)), gp75 (TRP-1) (Wang et al., *J. Exp. Med.*, 186:1131-1140 (1996)), tyrosinase (Wolfel et al., *Eur. J. Immunol.*, 24:759-764 (1994)), NY-ESO-1 (WO 99/18206) melanoma proteoglycan (Hellstrom et al., *J. Immunol.*, 130:1467-1472 (1983)), antigens of MAGE family (i.e., MAGE-1, 2, 3, 4, 6, and 12; Van der Bruggen et al., *Science*, 254:1643-1647 (1991)), antigens of BAGE family (Boel et al., *Immunity*, 2:167-175 (1995)), antigens of GAGE family (i.e., GAGE-1,2; Van den Eynde et al., *J. Exp. Med.*, 182:689-698 (1995)), antigens of RAGE family (i.e., RAGE-1; Gaugler et at., *Immunogenetics*, 44:323-330 (1996)), N-acetylglucosaminyltransferase-V (Guilloux et at., *J. Exp. Med.*, 183:1173-1183 (1996)), p15 (Robbins et al., *J. Immunol.* 154:5944-5950 (1995)), β-catenin (Robbins et al., *J. Exp. Med.*, 183:1185-1192 (1996)), MUM-1 (Coulie et al., *Proc. Natl. Acad. Sci. USA*, 92:7976-7980 (1995)), cyclin dependent kinase-4 (CDK4) (Wolfel et al., *Science*, 269:1281-1284 (1995)), p21 ras (Fossum et at., *Int. J. Cancer*, 56:40-45 (1994)), BCR-abl (Bocchia et al., *Blood*, 85:2680-2684 (1995)), p53 (Theobald et al., *Proc. Natl. Acad. Sci. USA*, 92:11993-11997 (1995)), p185 HER2/neu (Fisk et al., *J. Exp. Med.*, 181:2109-2117 (1995)), epidermal growth factor receptor (EGFR) (Harris et al., *Breast Cancer Res. Treat*, 29:1-2 (1994)), carcinoembryonic antigens (CEA) (Kwong et al., *J. Natl. Cancer Inst.*, 85:982-990 (1995) U.S. Pat. Nos. 5,756,103; 5,274,087; 5,571,710; 6,071,716; 5,698,530; 6,045,802; EP 263933; EP 346710; and, EP 784483); carcinoma-associated mutated mucins such as MUC-1 gene products (Jerome et al., *J. Immunol.*, 151:1654-1662 (1993)); EBNA gene products of EBV, for example, EBNA-1 gene product (Rickinson et al., *Cancer Surveys*, 13:53-80 (1992)); E7, E6 proteins of human papillomavirus (Ressing et al., *J. Immunol*, 154:5934-5943 (1995)); prostate specific antigens (PSA) (Xue et al., *The Prostate*, 30:73-78 (1997)); prostate specific membrane antigen (PSMA) (Israeli, et al., *Cancer Res.*, 54:1807-1811 (1994)); idiotypic epitopes or antigens, for example, immunoglobulin idiotypes or T cell receptor idiotypes (Chen et al., *J. Immunol.*, 153:4775-4787 (1994)); KSA (U.S. Pat. No. 5,348,887), NY-ESO-1 (WO 98/14464), and NY-BR-1 (WO 01/47959). Other suitable tumor antigens are known in the art.

Similarly, where the antigen is derived from an infectious agent such as a bacterium, virus, parasite or fungus, the host is preferably protected from infection by an organism expressing the antigen and/or the host acquires the ability to eliminate an existing infection. For example, where the antigen is the HIV gp120 protein or an immunogenic fragment derived therefrom, the host is preferably protected from infection by HIV and/or the host acquires the ability to eliminate HIV already existing in the host.

The chimeric nucleic acid molecule may further include a nucleic acid sequence encoding an immunostimulatory molecule. Many suitable immunostimulatory molecules are available to one of skill in the art including, for example, cytokines (e.g., interleukin-2 (IL-2), interleukin-12 (IL-12), and granulocyte-macrophage colony stimulating factor (GM-CSF)), co-stimulatory molecules (e.g., the B7 family of molecules such as B7.1 and B7.2), and/or other lymphokines that enhance the immune response. In certain embodiments of the current invention, the immunogenic polypeptide composition of the current invention includes both a CD36 binding/immunogen chimeric polypeptide and an immunostimulatory molecule, in admixture with a pharmaceutically acceptable diluent or carrier.

It is preferred that the nucleic acid sequences encoding the CD36 binding region and the antigen be operably linked so as to be expressed in a cell as a chimeric polypeptide. In one embodiment, the CD36 binding region(s) may be coupled to the amino terminus or carboxy terminus of the antigen coding region. Alternatively, the CD36 binding region may be coupled to a region within the antigen, provided that at least one immunologically effective epitope (i.e., an epitope capable of eliciting an immune response) and preferably all immunologically effective epitopes of the antigen are preserved. In a preferred embodiment, the fusion construct is constructed by ligating a polynucleotide encoding a CD36 binding region in frame to a polynucleotide encoding the antigen and expressing the ligated polynucleotide in a cell transfected with the polynucleotide.

It is also possible to generate the chimeric polypeptide by linking the CD36 binding region to the antigen indirectly through either a covalent or non-covalent association. Preferably, the linkage between the CD36 binding region and the antigen is covalent. Methods of performing such linkages are known in the art (see, for example, "Chemistry of Protein Conjugation and Crosslinking". 1991, Shans Wong, CRC Press, Ann Arbor). Suitable crosslinking agents known in the art include, for example, the homobifunctional agents glutaraldehyde, dimethyladipimidate and bis(diazobenzidine) and the heterobifunctional agents m-maleimidobenzoyl-N-hydroxysuccinimide and sulfo-m maleimidobenzoyl-N-hydroxysuccinimide. Other suitable agents are known in the art.

In one embodiment, indirect linkage of the CD36 binding region may be accomplished using a binding pair. For these embodiments, the CD36 binding region is coupled to a first binding pair member that is capable of binding under physiological conditions to a second binding pair member that is coupled to the antigen. Many suitable binding pairs, such as biotin and avidin, are known in the art. Preferably, the CD36 binding region is coupled to the amino terminus of the antigen-coding region.

In certain embodiments, the CD36 binding region/antigen chimeric polypeptides of the current invention are secreted from cells. It is preferred that the polypeptides are expressed in an immature form containing a signal sequence, which is cleaved during the secretion process. The signal sequence may be derived from either a prokaryote or a eukaryote. For example, a prokaryotic signal sequence may be used where eukaryotic post-translational modifications of the fusion polypeptide are not necessary to elicit an enhanced immune response against the antigen. For these situations, the chimeric polypeptides may be expressed and secreted in vitro in a bacterial host cell.

In certain embodiments, the signal sequence comprises an endoplasmic reticulum (ER)-targeting sequence and a signal peptidase (SP) sequence. Inclusion of these sequences typically results in secretion of the CD36 binding region/antigen chimeric polypeptides from cells transfected with a CD36 binding region/antigen chimeric polynucleotide of the current invention. In a preferred embodiment, the ER/SP sequences comprise amino acid residues 1-44 of TSP1 as shown in SEQ ID NO.: 7 and FIGS. 1B-K. Other ER/SP sequences and methods for identifying such sequences are known in the art (Goa et al., "Aids Res. and Human Retroviruses, 10: 1359 (1994)). In preferred embodiments, the ER/SP sequence is positioned 5' of the one or more nucleic acid sequences encoding a CD36 binding region and the one or more nucleic acid sequences encoding the antigen.

In another aspect, the present invention provides an isolated form of the chimeric CD36 binding/immunogen polynucleotide of the present invention, wherein a nucleic acid sequence encoding a CD36 binding region is ligated in frame to a nucleic acid sequence encoding an antigen. In one embodiment, the present invention provides a chimeric polynucleotide including a secretion signal sequence ligated upstream of the CD36 binding sequence which is ligated upstream of the antigen-coding sequence.

By "isolated" nucleic acid is intended a nucleic acid molecule, DNA or RNA, which has been removed from its native environment. Isolated DNA molecules include recombinant DNA molecules maintained in heterologous host cells or purified (partially or substantially) DNA molecules in solution. Isolated RNA molecules include in vivo, or in vitro RNA transcripts of the DNA molecules of the present invention. Isolated nucleic acid molecules according to the present invention further include such molecules produced synthetically. Recombinant DNA molecules contained in a vector are also considered isolated for the purposes of the present invention. The isolated nucleic acid molecules and expression vectors of the present invention may be constructed using standard recombinant techniques widely available to one skilled in the art. Such techniques may be found in common molecular biology references such as *Molecular Cloning: A Laboratory Manual* (Sambrook, et al., 1989, Cold Spring Harbor Laboratory Press), *Gene Expression Technology* (Methods in Enzymology, Vol. 185, edited by D. Goeddel, 1991. Academic Press, San Diego, Calif.), and *PCR Protocols: A Guide to Methods and Applications* (Innis, et al. 1990. Academic Press, San Diego, Calif.).

Figure 2A:
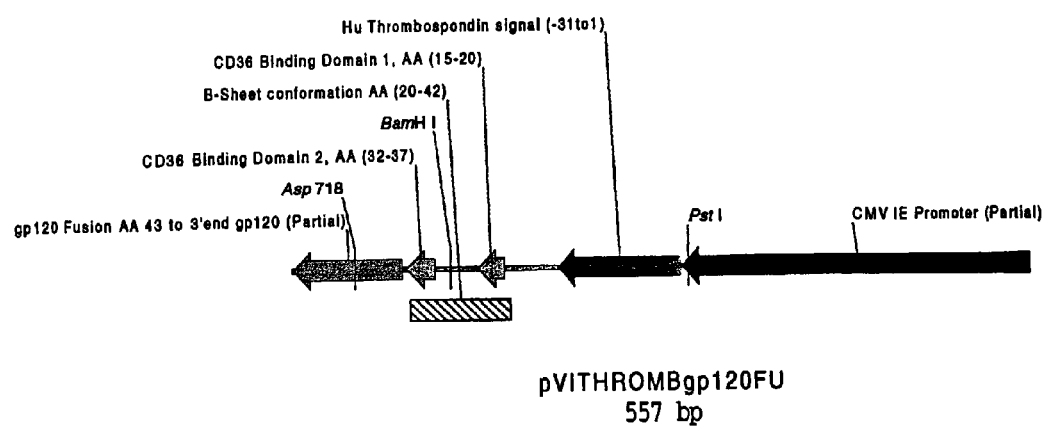
Figure 3:
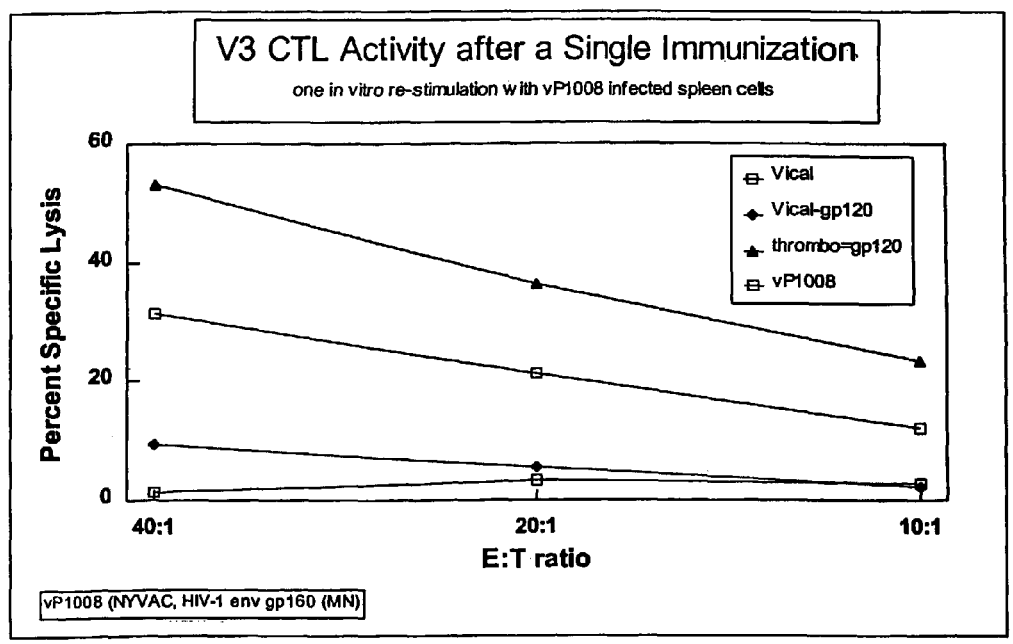
Figure 4:
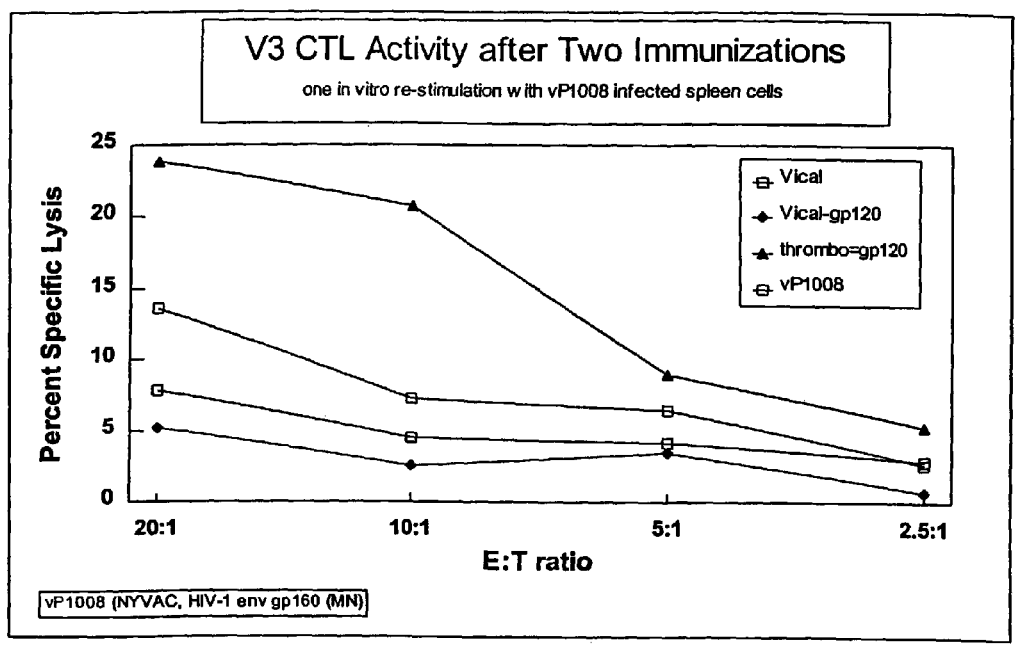
Figure 5:
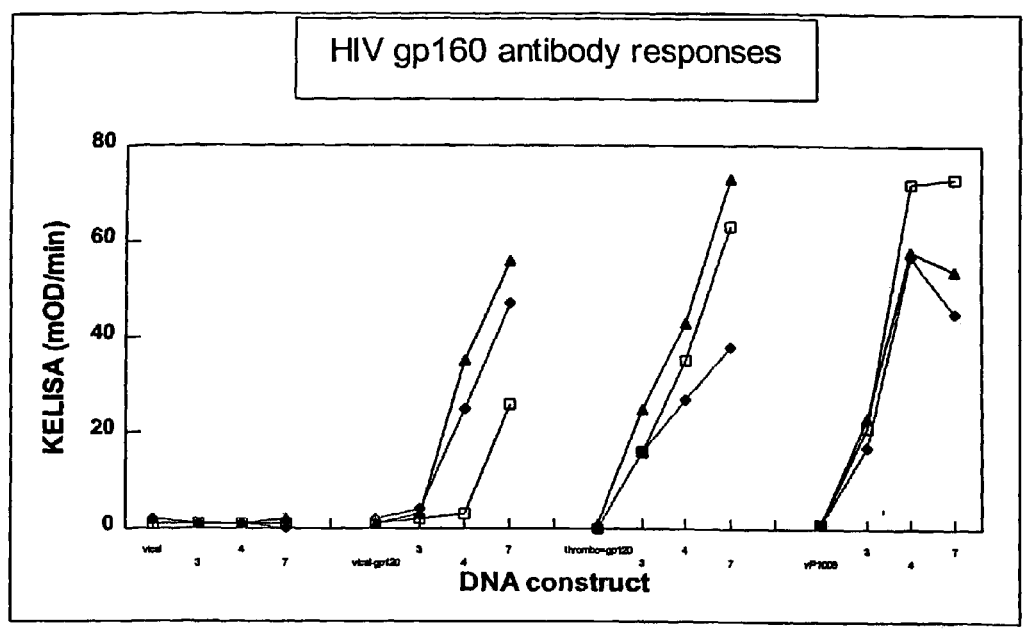
Figure 6:
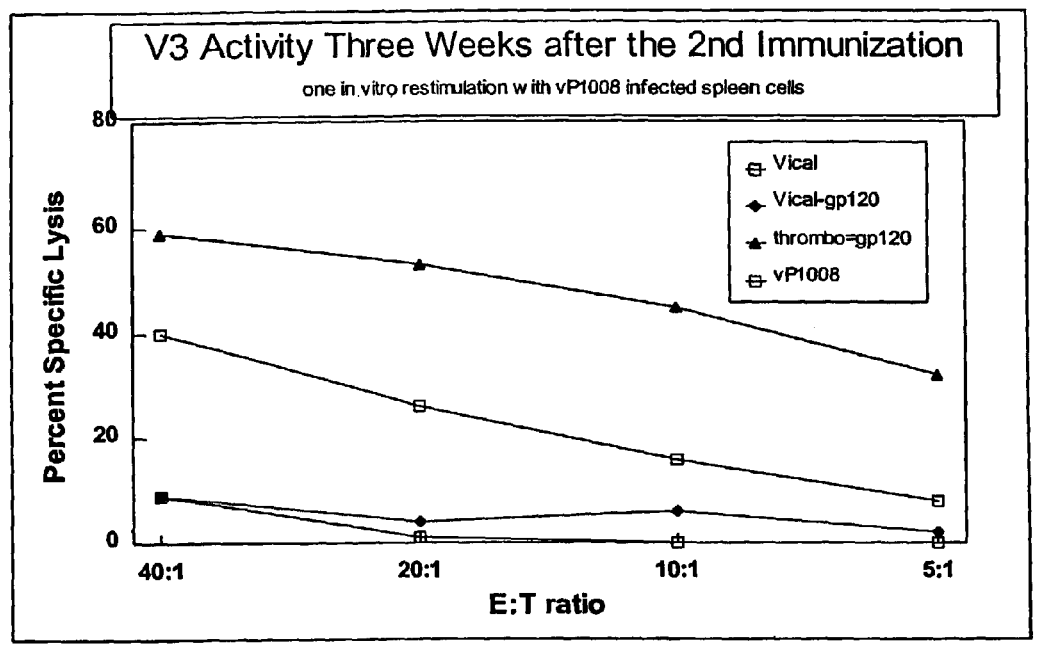
Figure 7:
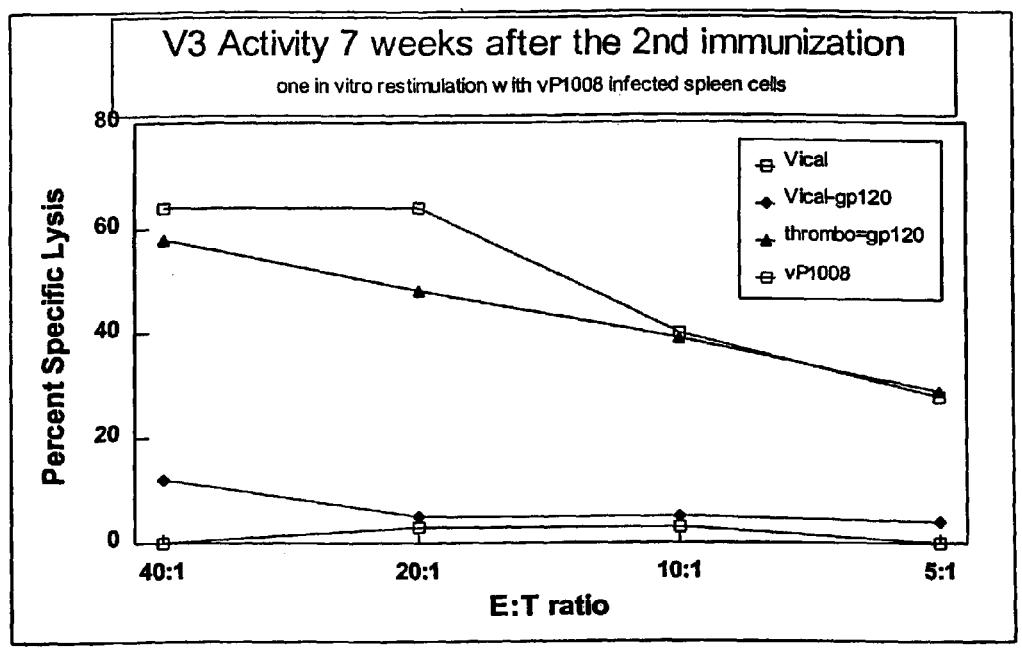

In preferred embodiments, the isolated nucleic acids of the current invention include a transcriptional regulatory region that is operatively-linked to the chimeric nucleic acid molecule. By "operatively linked" is meant transcription of the chimeric polynucleotide is affected by the activity of the transcriptional regulatory region. Preferably, the transcriptional regulatory region drives high-level gene expression in the target cell. The transcriptional regulatory region may comprise, for example, a promoter, enhancer, silencer, repressor element, or combinations thereof. A wide variety of promoters can be utilized for the current invention. Suitable transcriptional regulatory regions include, for example, the CMV promoter (i.e., the CMV-E1 promoter shown in FIGS. 2A and 2B); the SV40 late promoter; promoters from eukaryotic genes, such as the estrogen-inducible chicken ovalbumin gene, the interferon genes, the gluco-corticoid-inducible tyrosine aminotransferase gene, and the thymidine kinase gene; and the major early and late adenovirus gene promoters. Furthermore, as a large number of retroviruses are known that infect a wide range of eukaryotic host cells, the long terminal repeats (LTRs) frequently may also suffice as transcriptional regulatory regions. It is also possible to operably link the chimeric polynucleotide to a tissue- or cell-specific transcriptional regulatory region to affect expression of the chimeric polynucleotide in certain cells or tissues. As such, when the isolated CD36 binding/antigen polynucleotide is inserted into a cell, transcription of the chimeric polynucleotide is induced resulting in expression of the CD36 binding/antigen chimeric polypeptide.

The chimeric polynucleotides are preferably administered as part of an expression vector. The vectors can be either RNA or DNA, either prokaryotic or eukaryotic, and are typically of viral or plasmid origin. As such, the chimeric polynucleotide is inserted into an expression vector such that the polynucleotide is expressed when transformed into a host cell.

Expression vectors of the present invention include any vectors that function (i.e., direct gene expression) in recombinant cells of the present invention, including in bacterial, fungal, parasite, insect, animal, and plant cells. Preferred expression vectors of the present invention can direct gene expression in animal cells, preferably mammalian, most preferably human cells.

There are many methods and vectors available for expressing polynucleotides in cells. For instance, several types of mammalian expression systems are known in the art. (See e.g., Sambrook et al., "Expression of Cloned Genes in Mammalian Cells." In Molecular Cloning: A Laboratory Manual, 2nd ed. (1989)). Viral transduction methods may comprise the use of a recombinant DNA or an RNA virus comprising a nucleic acid sequence encoding the chimeric polypeptide to infect a cell, resulting in expression of the chimeric polypeptide. Suitable viral vectors include, for example, adenovirus, pox viruses (i.e., vaccinia or avipox), polio virus, and alphavirus, among others known in the art.

Examples of suitable retroviral vectors include, but are not limited to Moloney murine leukemia virus (MoMuLV), Harvey murine sarcoma virus (HaMuSV), murine mammary tumor virus (MuMTV), SIV, BIV, HIV and Rous Sarcoma Virus (RSV). A number of additional retroviral vectors can incorporate multiple genes. Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to Ψ2, PA317 and PA12, for example.

In a preferred embodiment, the viral vector is a poxvirus such as vaccinia virus (Smith, et al., 1983, *Gene*, 25 (1): 21-8; Moss, 1992, *Biotechnology*, 20: 345-62; Moss, 1992, *Curr. Top. Microbiol. Immunol.*, 158: 25-38; U.S. Pat. Nos. 5,364,773, 5,990,091, and 5,174,993). In certain embodiments, a highly attenuated strain of vaccinia, designated MVA, may be used as a vector (U.S. Pat. No. 5,185,146). A preferred vector is the NYVAC vector (U.S. Pat. Nos. 5,364,773 and 5,494,807). In other preferred embodiments, the poxvirus vector is ALVAC (1) or ALVAC (2), both of which are derived from canarypox virus (see, for example, U.S. Pat. Nos. 5,833,975 and 5,990,091; Tartaglia, et al., *J. Virol.* 67: 2370 (1993)). Fowlpox virus is another avipoxvirus that may also be used in practicing the present invention (see, for example, U.S. Pat. No. 5,766,599). Other suitable poxvirus vectors are known in the art.

In certain embodiments, the vector is a plasmid vector. Many plasmid expression vectors are known in the art and could be used with the current invention. In preferred embodiments, isolated nucleic acids are directly administered to an animal, virtually any expression vector that is effective in animal cells can be used. Preferred vectors where the isolated nucleic acids of the current invention are intended for NAVAC applications.

Bacterial vectors may also be used with the current invention. These vectors include, for example, *Shigella, Salmonella, Vibrio cholerae, Lactobacillus, Bacille Calmette Guérin* (BCG), and *Streptococcus* (See e.g., WO 88/6626; WO 90/0594; WO 91/13157; WO 92/1796; and WO 92/21376). In these bacterial vector embodiments of this invention, a chimeric CD36 binding/immunogen polynucleotide of the invention may be inserted into the bacterial genome, may remain in a free state, or may be carried on a plasmid (as described above). Other suitable vectors include the *E. coli* expression vector pUR278 and the glutathione S-transferase (GST) vector pGEX.

Other delivery techniques including DNA-ligand complexes, adenovirus-ligand-DNA complexes, direct injection of DNA, CaPO$_4$ precipitation, gene gun techniques, electroporation, liposomes and lipofection (Mulligan, R., 1993, *Science*, 260 (5110): 926-32) have also been demonstrated to be useful. Lipofection may be accomplished by encapsulating an isolated DNA molecule within a liposomal particle and contacting the liposomal particle with the cell membrane of the target cell. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form. Other suitable methods are available to one skilled in the art, and it is to be understood that the present invention may be accomplished using any of the available methods of transfection.

The current invention further provides isolated CD36 binding/immunogen chimeric polypeptides. The term "isolated" as used herein refers to the removal of a polypeptide from its natural environment and does not imply any specific level of purity of the polypeptide. Many methods are known in the art that can be used to prepare the CD36 binding/immunogen chimeric polypeptides. For example, the fusion polypeptides may be prepared as recombinant fusion polypeptides using the CD36 binding/immunogen expression polynucleotides and recombinant cell lines. The CD36 binding/immunogen chimeric polypeptides may also be prepared by covalently linking the CD36 binding region to the antigen using chemical cross-linking methods and cross-linking agents well-known in the art as described above. (see, for example, "Chemistry of Protein Conjugation and Crosslinking". 1991, Shans Wong, CRC Press, Ann Arbor).

In certain embodiments, the isolated polypeptides of the current invention include additional purification fusion polypeptide segments that assist in purification of the polypeptides. Suitable fusion segments include, among others, metal binding domains (e.g., a poly-histidine segment), immunoglobulin binding domains (e.g., Protein A; Protein G; T cell; B cell; Fc receptor or complement protein antibody-binding domains), sugar binding domains (e.g., a maltose binding domain), and/or a "tag" domain (e.g., at least a portion of α-galactosidase, a strep tag peptide, a T7 tag peptide, a Flag peptide, or other domains that can be purified using compounds that bind to the domain, such as monoclonal antibodies). Other suitable fusion segments are well known in the art.

In another aspect, the current invention includes recombinant cells and cell lines that express the CD36 binding/immunogen fusion polypeptides of the current invention. The recombinant cells and cell lines may be prokaryotic or preferably eukaryotic cells, that are transformed with one or more CD36 binding/immunogen expression vector. A cell can be "transformed," as the term is used in this specification, with a nucleic acid molecule, such as a recombinant expression vector, by any method by which a nucleic acid molecule can be introduced into the cell. Transformation techniques include, but are not limited to, transfection, infection, electroporation, microinjection, lipofection, adsorption, and protoplast fusion. Transformation may be stable or transient. A "cell line" refers to any immortalized recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained.

Suitable host cells include any cell that can be transformed with a nucleic acid molecule of the present invention, but are preferably a host cell from an organism to which an expressed CD36 binding/antigen chimeric polypeptide will be administered. Many such cells are available to the skilled artisan including, for example, primary cells such as fibroblasts or dendritic cells, Vero cells, non-tumorigenic mouse myoblast G8 cells (e.g., ATCC CRL 1246), K562 erythroleukemia cells, mouse NIH/3T3 cells, other fibroblast cell lines (e.g., human, murine, or chicken embryo fibroblast cell lines), myeloma cell lines, Chinese hamster ovary cells, LMTK31 cells, and/or HeLa cells. In one embodiment, the recombinant cell line is a myeloma cell line employing immunoglobulin promoters operatively linked to the chimeric polynucleotides of the current invention.

A recombinant cell of the current invention is preferably produced by transforming a host cell with one or more recombinant molecules, each comprising one or more chimeric polynucleotides of the current invention operatively linked to an expression vector containing one or more transcription control sequences, examples of which are disclosed herein. A recombinant cell of the present invention includes any cell transformed with at least one of any chimeric polynucleotide of the present invention. In a preferred embodiment of this aspect of the invention, the transformed host cells are immortalized mammalian cell lines capable of expressing high levels of CD36 binding/antigen chimeric polypeptides.

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of chimeric polynucleotides of the present invention include, but are not limited to, operatively linking the polynucleotides to high-copy number plasmids, integration of the polynucleotides into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation.

In another aspect, the current invention provides a method for producing a CD36 binding/antigen fusion polypeptide in a host cell. For this method, an isolated chimeric CD36 binding/antigen polynucleotide is introduced into an expression vector to produce a CD36 binding/antigen expression vector. The CD36 binding/antigen expression vector is then introduced into a host cell to produce a transformed host cell. The transformed host cell is then maintained under conditions suitable for the expression of CD36 binding/antigen chimeric polypeptide. Finally, the fusion polypeptide is collected.

Preferred host cells are described above. Effective culture conditions include, but are not limited to, effective media, bioreactor, temperature, pH, and oxygen conditions that permit protein production. An effective medium refers to any medium in which a cell is cultured to produce a fusion polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH, and oxygen conditions appropriate for a recombinant cell. Such culturing conditions are within the expertise of one of ordinary skill in the art. Depending on the vector and host system used for production, resultant polypeptides of the present invention can remain within the recombinant cell, be secreted into the fermentation medium or into a space between two cellular membranes (e.g., the periplasmic space in *E. coli*), or be retained on the outer surface of a cell or viral membrane.

The phrase "collecting the peptide", as well as similar phrases, refers to collecting the whole medium containing the fusion polypeptide and need not imply additional steps of separation or purification. Fusion polypeptides of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing, and differential solubilization. Fusion polypeptides of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The chimeric nucleic acids and polypeptides of the present invention may be administered to a host alone or in combination with another agent. In certain embodiments, the chimeric nucleic acid molecule or polypeptide is administered in a pharmaceutically acceptable carrier or diluent. Many pharmaceutically-acceptable carriers and diluents as well as methods for determining the route and quantities for administration are known in the art.

The term "pharmaceutically acceptable" means approved by a regulatory agency of the Federal or a state government or listed in the U.S. Pharmacopeia or other generally recognized pharmacopeia for use in animals, and more particularly in humans. The terms "carrier" and "carrier or diluent" refers to a diluent, adjuvant, excipient, or vehicle with which the therapeutic is administered. Carriers are well known in the art. For example, saline solutions and aqueous dextrose and glycerol solutions can be employed as liquid carriers, particularly for injectable solutions. Examples of suitable pharmaceutical carriers are described in "Remington's Pharmaceutical Sciences" by E. W. Martin.

In embodiments of the current invention wherein a polynucleotide is administered to an animal, certain preferred formulations are those used in NAVAC applications. The polynucleotide may be used in a naked/free form, free of any delivery vehicles. When administered in a naked/free form the polynucleotide can be simply diluted in a physiologically acceptable solution (such as sterile saline or sterile buffered saline) with or without a carrier. When present, the carrier preferably is isotonic, hypotonic, or weakly hypertonic, and has a relatively low ionic strength (i.e., a sucrose solution containing, for example, 20% sucrose).

Alternatively, the polynucleotide can be associated with agents that assist in cellular uptake (i.e., delivery vehicles). Delivery vehicles include, but are not limited to, anionic liposomes, polynucleotide and/or non-polynucleotide vector components, cationic lipids, microparticles, (e.g., gold microparticles), precipitating agents (e.g., calcium phosphate)) or any other transfection-facilitating agent.

In certain preferred embodiments, an immunogenic composition of the current invention is co-administered with an adjuvant. Typically, adjuvants used with the current invention are non-toxic and do not cause undesirable side effects. Examples of adjuvants that can be used with the current invention include, but are not limited to, aluminum hydroxide and aluminum phosphate, collectively commonly referred to as alum.

It is preferred that the chimeric nucleic acid or polypeptide induces or enhances the immune response of the host against the antigen. To accomplish this, an effective amount of an immunogenic composition comprising a chimera is administered to the host. Standard techniques may be used to determine an effective amount of the chimera to be administered. In particular, an effective amount may be determined by techniques well-known to those skilled in the medical or veterinary arts taking into consideration such factors as the immunogenicity of the antigen, the condition of the animal intended for administration (i.e., the weight, age, and general health of the animal), the mode of administration, and the type of formulation. The amount of immunogenic composition as well as a dosage regime may be adjusted to provide the optimum induction of an immune response. In preferred embodiments, the host is a mammal, most preferably a human.

Suitable routes of administration are many, as is known in the art. Such routes include, for example, mucosal (e.g., ocular, intranasal, oral, gastric, pulmonary, intestinal, rectal, vaginal, or urinary tract), parenteral (e.g., subcutaneous, intradermal, intramuscular, intravenous, or intraperitoneal), or intranodal routes. The administration may be by injection, oral administration, inhalation, transdermal application, rectal administration, or any other route of immunization that enables the modulation of an animal's immune system. In certain preferred embodiments, the administration is by injection. Certain preferred routes are those that are effective for NAVAC applications, such as intramuscular, and most preferably skin. The administration can be achieved in a single dose or repeated at intervals.

A particularly preferred method of administering the immunogenic compositions of the current invention is by a prime-boost protocol. Typically, an initial administration of a chimeric polynucleotide or polypeptide composition followed by a boost with the same immunogenic composition, will elicit an enhanced immune response (See e.g., WO 98/58956). Timing of the booster following the prime may be determined by a skilled artisan to provide optimum response.

The following examples describe and illustrate the methods and compositions of the invention. These examples are intended to be merely illustrative of the present invention, and not limiting thereof in either scope or spirit. Unless indicated otherwise, all percentages and ratios are by weight. Those skilled in the art will readily understand that variations of the materials, conditions, and processes described in these examples can be used.

Example 1

Preparation of Polynucleotide Constructs

This Example describes the preparation of a DNA construct encoding a chimeric polypeptide wherein the mature gp120 form of HIV-1 env is ligated to two CD36 binding domains of thrombospondin, and the insertion of the construct into an expression vector. The sequence for TSP1 was obtained from the National Center for Biotechnology Information (NCBI) (Genbank Accession # X14787; FIGS. 1B-K). As previously described, the TSP1-CD36 binding domains have been clearly defined as type 1 properdin-like repeats defined by the amino acid sequence CSVTCG. The antigen used in this Example is HIV gp120(mn) (Goa, F. et al., *Aids Res. and Human Retroviruses*, 10: 1359 (1994).

The chimeric polypeptide was constructed such that the TSP1 endoplasmic reticulum targeting signal and CD36 binding domain(s) were positioned at the $NH_2$-terminal end, such that the secreted polypeptide would retain the CD36 binding domains. Because the TSP1-CD36 binding domains are small (i.e., 6 amino acids) and the interaction with CD36 is believed to be conformation dependent, the binding domains were engineered to be expressed as in native TSP1 to retain proximal structural conformation.

The coding sequences for the engineered portion of the fusion protein were generated using overlapping oligonucleotides synthesized by Operon Technologies (Alameda, Calif.). The amino acid sequences of human TSP1 that were incorporated into the chimeric construct are shown below (numbers refer to amino acids in human TSP1):

TSP1 1-31: coding sequences for signal sequence
TSP1 32-44: coding sequences for signal peptidase cleavage
TSP1 447-452: coding sequences generated CD36 Binding Domain 1
TSP1 453-463: coding sequences for a Beta Sheet region
TSP1 504-511: CD36 Binding Domain 2

The joining Beta Sheet region between the CD36 binding domains of thrombospondin was retained in the construct because protein sequence analysis revealed both TSP1-CD36 domains were contained in regions of strong Beta Sheet conformation. To maintain conformational integrity, the spacer region engineered between Domain 1 and 2 also contained Beta Sheet conformation.

The TSP1 portion of the hybrid molecule was synthesized by overlapping and amplifying the oligonucleotides shown below:

```
HTHROM1A
                                          (SEQ ID NO.: 2)
ATCATCCTGCAGATGGGGCTGGCCTGGGGACTAGGCGTCCTGTTCCTGATG

CATGTGTGTGGCACCAACCGCATTCCAGAG

HTHROM2
                                          (SEQ ID NO.: 3)
AGACCCCTTGCGGGCGGCCCCGGTGAGTTCAAAGATGTCAAACACGCTGTT

GTCTCCGCCAGACTCTGGAATGCGGTTGGTGC

HTHROM3
                                          (SEQ ID NO.: 4)
GGGGCCGCCCGCAAGGGGTCTTCTTGTTCTGTGACATGTGGTGATGGTGTG

ATCACAAGGATCCGGCTCTGCAAC

HTHROM4
                                          (SEQ ID NO.: 5)
ATCATCGGTACCCCATAATAGACTGTGACCCACAATTTTTCGCTCCCTCCT

CCACAGGTGACAGAACAGTTGCAGAGCCGGATCCTTG
```

Primers HTHROM1A and HTHROM2 overlap one another and primer HTHROM3 overlaps HTHROM2 and HTHROM4. Primer HTHROM3 overlaps primer HTHROM2 and HTHROM4. To generate the full coding sequence of the TSP1 portion of the hybrid, the primers were subjected to three minutes at 95° C. (denaturation), three minutes at 50° C. (annealing) and 10 minutes at 72° C. (extension). The resultant fragment representing the full-length product was gel purified and further purified by PCR using primers HTHROM1A and HTRHOM4 for 26 cycles at 94° C. for 30 seconds followed by 72° C. for 60 seconds. The resulting fragment was cloned and confirmed to be correct by DNA sequencing.

Primer HTHROM1A contains a Pst I restriction site (CTG-CAG) and primer HTHROM4 contains an Asp718 restriction site (GGTACC). These were used to position the TSP1 portion of the chimera upstream and in-frame with the HIV gp120 portion of the hybrid (the antigen) as shown below.

The HIV gp120 coding sequences used for the engineered fusion were assessed using published methods to identify the ER targeting signal sequence so it could be eliminated from the sequences used to express gp120 in the final fusion construct (Goa et al., 1994). Signal sequences in gp120 were identified as amino acids 1-21. These amino acids were not included in the chimeric construct. For fusions where CD36 binding domains are upstream of the antigen of interest, it is essential to remove all intervening cleavage sequences (i.e., signal peptidase sequences) between the CD36 binding domains and the antigen of interest.

For cloning purposes, the TSP1 portion of the hybrid was manipulated using the Pst I and Asp718 restriction sites. This 250 bp Pst-I Asp718 fragment containing the engineered CD36 binding domains, including sequences encoding 13 amino acids of the 5'end of gp120 (up to Asp718 restriction site), was directionally cloned using the Pst I/Asp718 sites into a prepared eukaryotic expression vector for NAVAC.

The engineered fragment was inserted into the expression vector in the proper orientation and in-frame with the Asp718 restriction site in the gp120 sequences. This resulted in a continuous reading frame from the TSP1 signal through the CD36 binding domains terminating at the gp120 3' carboxy terminus. The sequence was confirmed by DNA sequencing to ensure retention of the appropriate reading frame. The construct was designated thrombo=gp120 (FIGS. 2A and 2B). Large quantities of purified thrombo=gp120 were prepared using Qiagen Giga Preparations (endotoxin free) as per manufacturer instructions for NAVAC (Qiagen Inc. Valencia, Calif.).

Example 2

Analysis of Immunogenicity

This Example provides an analysis of the immunogenicity of thrombo=gp120 in mice. Mice were immunized once by an intramuscular (i.m.) route with 100 ug of DNA plasmid thrombo=gp120 expressing the TSP1-CD36 binding domain-gp120 fusion, plasmid vical gp120 expressing only gp120, or control plasmid in 0.1 ml of PBS. As a positive control mice were immunized with a recombinant poxvirus vP1008 (NYVAC-env; U.S. Pat. No. 5,494,807). Mice received two immunizations three weeks apart.

Both cell-mediated immunity (i.e. cytotoxic T-Cell (CTL) activity) and humoral antibody responses were analyzed in the study. For CTL activity, pooled spleen cells of three mice from each experimental group were restimulated in vitro with naive syngeneic spleen cells infected with vp1008 (HIV MN env). After 6 days, the spleen cells were assayed against P815 target cells pulsed with V3 epitope peptide (peptide 121). Specific cytotoxicity was calculated as the difference in cytotoxicity between peptide-pulsed P815 targets and P815 targets with no peptide pulse. Data for the CTL analysis is expressed as percent specific lysis (i.e. difference between HIV epitope peptide pulsed and un-pulsed targets) at various effector:Target (E:T) ratios. This analysis of CTL utilized Chromium-51 release assays (reviewed in Brunner, et al., "Quantitative assay of lytic action of immune cells on Cr-51 labeled allogenic target cells in vivo; inhibition by isoantibody and by drugs," *Immunology,* 14:181 (1968)).

Humoral antibody responses were analyzed by bleeding three mice from each group at the appropriate time point. Serum samples were collected at appropriate timepoints from representative mice of both test and control groups, using a retroorbital plexis procedure (McGuill, M. W. and Rowan A. N. Biological Effects of Blood Loss: implications for sampling volumes and techniques. I.L.A.R. News 31: 4 (1989)) The initial bleed (week 0) was prior to the initial immunization and the (week 3) bleed was just prior the second immunization. Individual sera from each mouse was diluted 1:400 and assayed by kinetics ELISA for antibodies against recombinant HIV MN/BRU envelope glycoprotein (PMS-France) (Cox, et al., *J. Natl. Cancer Inst.* 71:973 (1983); and Holbrook, et al. *Cancer Res.* 43:4019 (1983)).

FIGS. 3 and 4 summarize results of CTL analysis for this experiment. Three weeks after the initial immunization, CTL activity was not detected in mice immunized with control plasmid containing no gp120 sequences or vical gp120. In contrast, strong CTL responses were generated by mice immunized with DNA plasmid thrombo=gp120 (FIG. 3). The CTL responses elicited by this plasmid exceeded CTL responses generated by an optimal dose of vP1008 (NYVAC-env) given by the optimal intraperitoneal route. Three weeks after the second immunization, mice immunized with plasmid gp120 still had no detectable CTL activity (FIG. 4). Mice immunized with thrombo=gp120 maintained the strong CTL response seen after the first immunization.

Analysis of antibody response induced by the experimental samples confirmed that thrombo=gp120 constructs were effective at eliciting an immune response against gp120. Anti-HIV envelope glycoprotein antibody assays were performed on samples collected at 0, 3, 4, and 7 weeks after the start of the experiment (i.e. time of initial immunization). The strongest, most reliable responses were generated by mice immunized with thrombo-gp120 and recombinant poxvirus vp1008 (FIG. 5). In fact, no antibody responses were detected in mice after one immunization with control plasmid gp120. However, all three mice immunized one time only with thrombo=gp120 generated an antibody response. Antibody levels were similar to levels generated after immunization one time with vP1008.

Example 3

Further Analysis of Immunogenicity

This Example provides an analysis of the immunogenicity of thrombo=gp120 in mice that is a repeat of the analysis of Example 2 carried out for longer time periods. Immunizations and CTL and antibody assays were performed as described in Example 2. For this experiment, CTL analysis was performed at both 3 weeks and 7 weeks after the second immunization.

Three weeks after the second immunization, mice immunized with plasmid vical gp120 had no CTL activity above control levels (FIG. 6, Table I). However, mice immunized with thrombo=gp120 generated excellent CTL activity comparable to that generated with vP1008. Seven weeks after the second immunization mice immunized with vical gp120 showed a week CTL response (FIG. 7, Table II). However, mice immunized with thrombo=gp120 showed a strong CTL response.

TABLE I

Specific Lysis (CTL) three weeks after primary immunization

| TEST ARTICLE | E:T | % SPECIFIC LYSIS |
|---|---|---|
| Negative control plasmid | 40:1 | −5.4 |
| Negative control plasmid | 20:1 | −0.6 |
| Negative control plasmid | 10:1 | 0.5 |
| Negative control plasmid | 5:1 | −0.7 |
| Gp120 | 40:1 | −1.0 |
| Gp120 | 20:1 | 2.3 |
| Gp120 | 10:1 | 1.2 |
| Gp120 | 5:1 | 1.4 |
| Thromb = gp120 | 40:1 | 8.1 |
| Thromb = gp120 | 20:1 | 13.1 |
| Thromb = gp120 | 10:1 | 10.0 |
| Thromb = gp120 | 5:1 | 0.7 |
| VP1008 positive control | 40:1 | 17.7 |
| VP1008 positive control | 20:1 | 10.5 |
| VP1008 positive control | 10:1 | 4.1 |
| VP1008 positive control | 5:1 | 1.5 |

TABLE II

Specific CTL lysis, three and seven weeks after the second immunization

| TEST ARTICLE | E:T | % LYSIS WK 3 | % LYSIS WK 7 |
|---|---|---|---|
| Negative control plasmid | 40:1 | 8.9 | 0 |
| Negative control plasmid | 20:1 | 1.0 | 3.0 |
| Negative control plasmid | 10:1 | −0.1 | 2.6 |
| Negative control plasmid | 5:1 | −0.6 | 0.1 |
| gp120 | 40:1 | 9.0 | 12.4 |
| gp120 | 20:1 | 4.1 | 4.6 |
| gp120 | 10:1 | 5.9 | 5.3 |
| gp120 | 5:1 | 1.6 | 4.1 |
| Thromb = gp120 | 40:1 | 59.1 | 58.4 |
| Thromb = gp120 | 20:1 | 53.3 | 47.6 |
| Thromb = gp120 | 10:1 | 44.6 | 38.8 |
| Thromb = gp120 | 5:1 | 31.9 | 28.5 |
| vP1008 positive control | 40:1 | 40.3 | 64.4 |
| vP1008 positive control | 20:1 | 26.3 | 64.4 |
| vP1008 positive control | 10:1 | 15.7 | 40.2 |
| vP1008 positive control | 5:1 | 7.6 | 27.5 |

Figure 8:
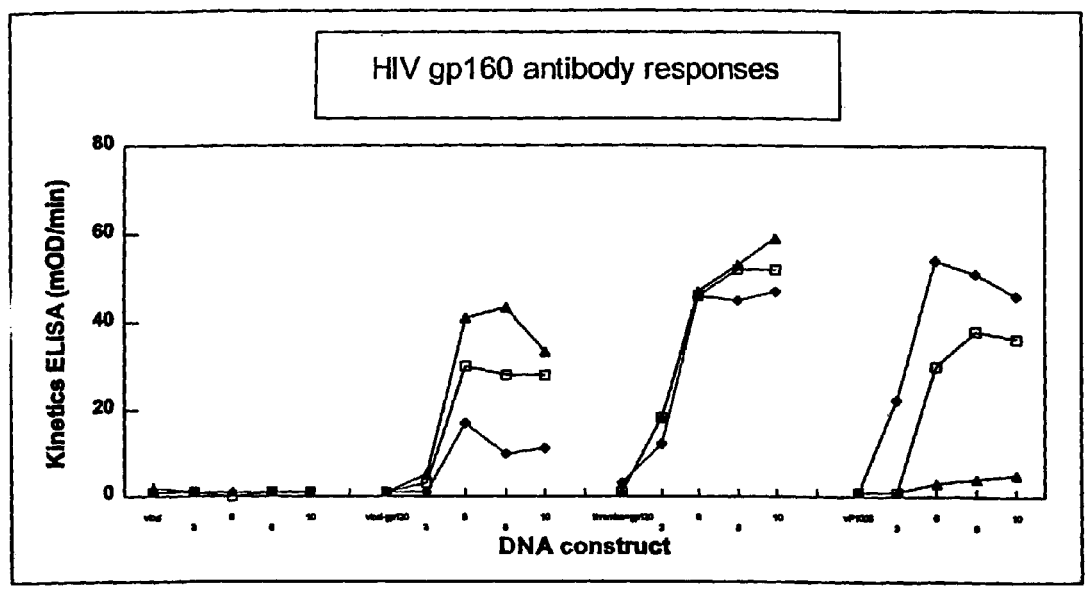

Antibody measurements confirmed that thrombo=gp120 induced a strong immunological response against gp120. All three mice immunized with thrombo=gp120 generated a strong antibody response after only one immunization (FIG. 8). In fact, when averages of three mice for each experimental group were calculated, highest titers of anti-gp120 antibodies were obtained following the initial immunization with either DNA plasmid thrombo=gp120 or the recombinant poxvirus vector pV1008 (Table III).

Antibody responses following the second immunization were also evaluated (week 4, 6, 8, 10 of FIG. 8 and Table III). The strong antibody response of mice immunized with plasmid thrombo=gp120 continued to escalate after the second immunization and continued throughout the study to show a stronger antibody titer than positive control vP1008.

TABLE III

Kinetics ELISA (mOD/min)

| | WEEK | | | | | |
|---|---|---|---|---|---|---|
| Test article | 0 | 3 | 4 | 6 | 8 | 10 |
| Negative control | 1 | 1 | 1.6 | 0.6 | 1 | 1 |
| gp120 | 1 | 3 | 22.7 | 29.3 | 27 | 24 |
| Thromb = gp120 | 1.7 | 16 | 36.3 | 46.3 | 50 | 52.6 |
| vP1008 | 1 | 8 | 21.6 | 29 | 31 | 29 |

The results of Examples 2 and 3 demonstrate that significant enhancement of both a cell-mediated and humoral immune response against HIV gp120, is obtained by coupling HIV gp120 with the TSP1-CD36 binding domain. Not to be limited by theory, it is believed that these results are related to the proposed mode of immunological enhancement, (i.e., APC Targeting), as other similar constructions expressing the identical version of gp120 as a fusion with other various targeting domains have failed to enhance responses. These results suggest that the resultant immunological enhancement is not simply associated with non-specific effects of altered expression and or persistence (i.e., half-life) of gp120 expressed as a fusion product.

This method of enhancing immune responses by targeting the antigen of interest to APC's can be applied to virtually any immunological target of interest, including those important for both infectious, and neoplastic diseases.

Throughout this application, various patents, publications, books, and nucleic acid and amino acid sequences have been cited. The entireties of each of these patents, publications, books, and sequences are hereby incorporated by reference into this application.

What is claimed is:

1. An isolated nucleic acid molecule encoding an immunogenic chimeric polypeptide, the nucleic acid molecule comprising at least a first nucleic acid sequence positioned upstream of and in frame with a second nucleic acid sequence, wherein:
the first nucleic acid sequence encodes two domains comprising the amino acid sequence CSVTCG (SEQ ID NO: 11) separated by a spacer region of about 11 amino acids; and,
the second nucleic acid sequence encodes at least one tumor antigen or an antigen derived from an infectious agent.

2. The isolated nucleic acid molecule of claim 1 wherein the spacer region has a beta sheet conformation.

3. The isolated nucleic acid molecule of claim 2 wherein the spacer amino acids comprise DGVITRIRLCN (SEQ ID NO: 1).

4. The isolated nucleic acid molecule of claim 1 further encoding a signal nucleic acid sequence consisting essentially of an endoplasmic reticulum signal sequence and a signal peptidase cleavage sequence.

5. The isolated nucleic acid molecule of claim 1 wherein the infectious agent is selected from the group consisting of a bacterium, a parasite, a virus, a fungus, and a cancerous cell.

6. The isolated nucleic acid molecule of claim 5 wherein second nucleic acid sequence encodes a gp120 polypeptide or immunogenic fragment thereof.

7. The isolated nucleic acid molecule of claim 1 or 5 further comprising a transcriptional regulatory region operably linked to at least one of the nucleic acid sequences.

8. The isolated nucleic acid molecule of claim 7 wherein said transcriptional control region is the CMV promoter.

9. An immunogenic composition for generating an immune response in a host, the composition comprising a nucleic acid molecule of claim 1 or 5.

10. An immunogenic composition for generating an immune response in a host, the composition comprising a nucleic acid molecule of claim 6.

11. An immunogenic composition for generating an immune response in a host, the composition comprising a nucleic acid molecule of claim 7.

12. An immunogenic composition for generating an immune response in a host, the composition comprising a nucleic acid molecule of claim 8.

13. The nucleic acid molecule of claim 1 wherein the first nucleic acid sequence encodes at least the amino acid sequence of SEQ ID NO.: 10.

* * * * *

SEQUENCE LISTING

<160> NUMBER OF SEQ ID NOS: 11

<210> SEQ ID NO 1
<211> LENGTH: 11
<212> TYPE: PRT
<213> ORGANISM: Homo sapiens

<400> SEQUENCE: 1

Asp Gly Val Ile Thr Arg Ile Arg Leu Cys Asn
1               5                   10

<210> SEQ ID NO 2
<211> LENGTH: 81
<212> TYPE: DNA

```
<213> ORGANISM: Artificial Sequence
<220> FEATURE:
<223> OTHER INFORMATION: Homo sapiens

<400> SEQUENCE: 2
atcatcctgc agatggggct ggcctgggga ctaggcgtcc tgttcctgat gcatgtgtgt    60
ggcaccaacc gcattccaga g                                              81

<210> SEQ ID NO 3
<211> LENGTH: 83
<212> TYPE: DNA
<213> ORGANISM: Artificial Sequence
<220> FEATURE:
<223> OTHER INFORMATION: Homo sapiens

<400> SEQUENCE: 3 agacccttg cgggcggccc cggtgagttc aaagatgtca acacgctgt tgtctccgcc      60 agactctgga atgcggttgg tgc                                            83

<210> SEQ ID NO 4
<211> LENGTH: 75
<212> TYPE: DNA
<213> ORGANISM: Artificial Sequence
<220> FEATURE:
<223> OTHER INFORMATION: Homo sapiens

<400> SEQUENCE: 4
ggggccgccc gcaaggggtc ttcttgttct gtgacatgtg gtgatggtgt gatcacaagg    60
atccggctct gcaac                                                     75

<210> SEQ ID NO 5
<211> LENGTH: 88
<212> TYPE: DNA
<213> ORGANISM: Artificial Sequence
<220> FEATURE:
<223> OTHER INFORMATION: Homo sapiens

<400> SEQUENCE: 5
atcatcggta ccccataata gactgtgacc cacaattttt cgctccctcc tccacaggtg    60
acagaacagt tgcagagccg gatccttg                                       88

<210> SEQ ID NO 6
<211> LENGTH: 5722
<212> TYPE: DNA
<213> ORGANISM: Homo sapiens

<400> SEQUENCE: 6
ggacgcacag gcattccccg cgcccctcca gccctcgccg ccctcgccac cgctcccggc    60
cgccgcgctc cggtacacac aggatccctg ctgggcacca acagctccac catggggctg   120
gcctggggac taggcgtcct gttcctgatg catgtgtgtg gcaccaaccg cattccagag   180
tctggcggag acaacagcgt gtttgacatc tttgaactca ccggggccgc ccgcaagggg   240
tctgggcgcc gactggtgaa gggccccgac ccttccagcc cagctttccg catcgaggat   300
gccaacctga tcccctgt gcctgatgac aagttccaag acctggtgga tgctgtgcgg    360
gcagaaaagg gtttcctcct tctggcatcc ctgaggcaga tgaagaagac ccggggcacg   420
ctgctggccc tggagcggaa agaccactct ggccaggtct tcagcgtggt gtccaatggc   480
aaggcgggca cctggaccct cagcctgacc gtccaaggaa agcagcacgt ggtgtctgtg   540
gaagaagctc tcctggcaac cggccagtgg aagagcatca ccctgtttgt gcaggaagac   600
```

```
agggcccagc tgtacatcga ctgtgaaaag atggagaatg ctgagttgga cgtccccatc     660
caaagcgtct tcaccagaga cctggccagc atcgccagac tccgcatcgc aaagggggc      720 gtcaatgaca atttccaggg ggtgctgcag aatgtgaggt ttgtctttgg aaccacacca     780
gaagacatcc tcaggaacaa aggctgctcc agctctacca gtgtcctcct caccccttgac    840 aacaacgtgg tgaatggttc cagccctgcc atccgcacta actacattgg ccacaagaca     900
aaggacttgc aagccatctg cggcatctcc tgtgatgagc tgtccagcat ggtcctggaa     960
ctcaggggcc tgcgcaccat tgtgaccacg ctgcaggaca gcatccgcaa agtgactgaa    1020
gagaacaaag agttggccaa tgagctgagg cggcctcccc tatgctatca aacggagtt     1080 cagtacagaa ataacgagga atggactgtt gatagctgca ctgagtgtca ctgtcagaac    1140
tcagttacca tctgcaaaaa ggtgtcctgc cccatcatgc cctgctccaa tgccacagtt    1200
cctgatggag aatgctgtcc tcgctgttgg cccagcgact ctgcggacga tggctggtct    1260
ccatggtccg agtggacctc ctgttctacg agctgtggca atggaattca gcagcgcggc    1320
cgctcctgcg atagcctcaa caaccgatgt gagggctcct cggtccagac acggacctgc    1380
cacattcagg agtgtgacaa agatttaaa caggatggtg gctggagcca ctggtccccg    1440
tggtcatctt gttctgtgac atgtggtgat ggtgtgatca aaggatccg gctctgcaac    1500 tctcccagcc cccagatgaa tgggaaaccc tgtgaaggcg aagcgcggga gaccaaagcc    1560
tgcaagaaag acgcctgccc catcaatgga ggctgggtc cttggtcacc atgggacatc    1620
tgttctgtca cctgtggagg aggggtacag aaacgtagtc gtctctgcaa caaccccgca    1680
ccccagtttg gaggcaagga ctgcgttggt gatgtaacag aaaaccagat ctgcaacaag    1740
caggactgtc caattgatgg atgcctgtcc aatccctgct tgccggcgt gaagtgtact    1800 agctaccctg atggcagctg gaaatgtggt gcttgtcccc ctggttacag tggaaatggc    1860
atccagtgca cagatgttga tgagtgcaaa gaagtgcctg atgcctgctt caaccacaat    1920
ggagagcacc ggtgtgagaa cacggacccc ggctacaact gcctgccctg ccccccacgc    1980
ttcaccggct cacagccctt cggccagggt gtcgaacatg ccacggccaa caaacaggtg    2040
tgcaagcccc gtaaccctg cacggatggg acccacgact gcaacaagaa cgccaagtgc    2100
aactacctgg ccactatag cgaccccatg taccgctgcg agtgcaagcc tggctacgct    2160
ggcaatggca tcatctgcgg ggaggacaca gacctggatg gctggccaa tgagaacctg    2220 gtgtgcgtgg ccaatgcgac ttaccactgc aaaaaggata attgccccaa ccttcccaac    2280
tcagggcagg aagactatga caaggatgga attggtgatg cctgtgatga tgacgatgac    2340
aatgataaaa ttccagatga cagggacaac tgtccattcc attacaaccc agctcagtat    2400
gactatgaca gagatgatgt gggagaccgc tgtgacaact gtccctacaa ccacaaccca    2460
gatcaggcag acacagacaa caatgggaa ggagacgcct gtgctgcaga cattgatgga    2520
gacggtatcc tcaatgaacg ggacaactgc cagtacgtct acaatgtgga ccagagagac    2580
actgatatgg atggggttgg agatcagtgt gacaattgcc ccttggaaca caatccggat    2640
cagctggact ctgactcaga ccgcattgga gatacctgtg acaacaatca ggatattgat    2700
gaagatggca ccagaacaa tctggacaac tgtccctatg tgcccaatgc aaccaggct    2760 gaccatgaca agatggcaa gggagatgcc tgtgaccacg atgatgacaa cgatggcatt    2820
cctgatgaca aggacaactg cagactcgtg cccaatcccg accagaagga ctctgacggc    2880
gatggtcgag gtgatgcctg caaagatgat tttgaccatg acagtgtgcc agacatcgat    2940
```

```
gacatctgtc ctgagaatgt tgacatcagt gagaccgatt tccgccgatt ccagatgatt   3000
cctctggacc ccaaagggac atcccaaaat gaccctaact gggttgtacg ccatcagggt   3060
aaagaactcg tccagactgt caactgtgat cctggactcg ctgtaggtta tgatgagttt   3120
aatgctgtgg acttcagtgg caccttcttc atcaacaccg aaagggacga tgactatgct   3180
ggatttgtct ttggctacca gtccagcagc cgcttttatg ttgtgatgtg gaagcaagtc   3240
acccagtcct actgggacac caaccccacg agggctcagg gatactcggg cctttctgtg   3300
aaagttgtaa actccaccac agggcctggc gagcacctgc ggaacgccct gtggcacaca   3360
ggaaacaccc ctggccaggt gcgcaccctg tggcatgacc ctcgtcacat aggctggaaa   3420
gatttcaccg cctacagatg gcgtctcagc cacaggccaa gacgggtttt cattagagtg   3480
gtgatgtatg aagggaagaa aatcatggct gactcaggac ccatctatga taaaacctat   3540
gctggtggta gactagggtt gtttgtcttc tctcaagaaa tggtgttctt ctctgacctg   3600
aaatacgaat gtagagatcc ctaatcatca aattgttgat tgaaagactg atcataaacc   3660
aatgctggta ttgcaccttc tggaactatg ggcttgagaa acccccagg atcacttctc    3720 cttggcttcc ttcttttctg tgcttgcatc agtgtggact cctagaacgt gcgacctgcc   3780
tcaagaaaat gcagttttca aaaacagact catcagcatt cagcctccaa tgaataagac   3840
atcttccaag catataaaca attgctttgg tttccttttg aaaaagcatc tacttgcttc   3900
agttgggaag gtgcccattc cactctgcct ttgtcacaga gcagggtgct attgtgaggc   3960
catctctgag cagtggactc aaaagcattt tcaggcatgt cagagaaggg aggactcact   4020
agaattagca aacaaaacca ccctgacatc ctccttcagg aacacgggga gcagaggcca   4080
aagcactaag ggagggcgc atacccgaga cgattgtatg aagaaaatat ggaggaactg    4140
ttacatgttc ggtactaagt cattttcagg ggattgaaag actattgctg gatttcatga   4200
tgctgactgg cgttagctga ttaacccatg taaataggca cttaaataga agcaggaaag   4260
ggagacaaag actggcttct ggacttcctc cctgatcccc acccttactc atcaccttgc   4320
agtggccaga attagggaat cagaatcaaa ccagtgtaag gcagtgctgg ctgccattgc   4380
ctggtcacat tgaaattggt ggcttcattc tagatgtagc ttgtgcagat gtagcaggaa   4440
aataggaaaa cctaccatct cagtgagcac cagctgcctc ccaaaggagg ggcagccgtg   4500
cttatatttt tatggttaca atggcacaaa attattatca acctaactaa acattcctt    4560 ttctcttttt tccgtaatta ctaggtagtt ttctaattct ctcttttgga agtatgattt   4620
ttttaaagtc tttacgatgt aaaatattta tttttactt attctggaag atctggctga    4680
aggattattc atggaacagg aagaagcgta aagactatcc atgtcatctt tgttgagagt   4740
cttcgtgact gtaagattgt aaatacagat tatttattaa ctctgttctg cctggaaatt   4800
taggcttcat acggaaagtg tttgagagca agtagttgac atttatcagc aaatctcttg   4860
caagaacagc acaaggaaaa tcagtctaat aagctgctct gccccttgtg ctcagagtgg   4920
atgttatggg attccttttt tctctgtttt atcttttcaa gtggaattag ttggttatcc   4980
atttgcaaat gttttaaatt gcaagaaag ccatgaggtc ttcaatactg ttttaccccca    5040 tcccttgtgc atatttccag gggagaaggaa agcatataca cttttttctt tcattttttcc   5100 aaaagagaaa aaaatgacaa aaggtgaaac ttacatacaa atattacctc atttgttgtg   5160
tgactgagta aagaattttt ggatcaagcg gaaagagttt aagtgtctaa caaacttaaa   5220
gctactgtag tacctaaaaa gtcagtgttg tacatagcat aaaaactctg cagagaagta   5280
ttcccaataa ggaaatagca ttgaaatgtt aaatacaatt tctgaaagtt atgttttttt   5340
```

```
tctatcatct ggtataccat tgctttattt ttataaatta ttttctcatt gccattggaa    5400
tagaatattc agattgtgta gatatgctat ttaaataatt tatcaggaaa tactgcctgt    5460
agagttagta tttctatttt tatataatgt ttgcacactg aattgaagaa ttgttggttt    5520
tttctttttt ttgtttttt ttttttttt ttttttttg cttttgacct cccatttta     5580 ctatttgcca ataccttttt ctaggaatgt gctttttttt gtacacattt ttatccattt    5640
tacattctaa agcagtgtaa gttgtatatt actgtttctt atgtacaagg aacaacaata    5700
aatcatatgg aaatttatat tt                                             5722

<210> SEQ ID NO 7
<211> LENGTH: 1169
<212> TYPE: PRT
<213> ORGANISM: Homo sapiens

<400> SEQUENCE: 7

Met Gly Leu Ala Trp Gly Leu Gly Val Leu Phe Leu Met His Val Cys
1               5                   10                  15

Gly Thr Asn Arg Ile Pro Glu Ser Gly Gly Asp Asn Ser Val Phe Asp
                20                  25                  30

Ile Phe Glu Leu Thr Gly Ala Ala Arg Lys Gly Ser Gly Arg Arg Leu
            35                  40                  45

Val Lys Gly Pro Asp Pro Ser Ser Pro Ala Phe Arg Ile Glu Asp Ala
        50                  55                  60

Asn Leu Ile Pro Pro Val Pro Asp Asp Lys Phe Gln Asp Leu Val Asp
65                  70                  75                  80

Ala Val Arg Ala Glu Lys Gly Phe Leu Leu Leu Ala Ser Leu Arg Gln
                85                  90                  95

Met Lys Lys Thr Arg Gly Thr Leu Leu Ala Leu Glu Arg Lys Asp His
                100                 105                 110

Ser Gly Gln Val Phe Ser Val Val Ser Asn Gly Lys Ala Gly Thr Leu
            115                 120                 125

Asp Leu Ser Leu Thr Val Gln Gly Lys Gln His Val Val Ser Val Glu
        130                 135                 140

Glu Ala Leu Leu Ala Thr Gly Gln Trp Lys Ser Ile Thr Leu Phe Val
145                 150                 155                 160

Gln Glu Asp Arg Ala Gln Leu Tyr Ile Asp Cys Glu Lys Met Glu Asn
                165                 170                 175

Ala Glu Leu Asp Val Pro Ile Gln Ser Val Phe Thr Arg Asp Leu Ala
                180                 185                 190

Ser Ile Ala Arg Leu Arg Ile Ala Lys Gly Gly Val Asn Asp Asn Phe
            195                 200                 205

Gln Gly Val Leu Gln Asn Val Arg Phe Val Phe Gly Thr Thr Pro Glu
        210                 215                 220

Asp Ile Leu Arg Asn Lys Gly Cys Ser Ser Thr Ser Val Leu Leu Thr
225                 230                 235                 240

Leu Asp Asn Asn Val Val Asn Gly Ser Ser Pro Ala Ile Arg Thr Asn
                245                 250                 255

Tyr Ile Gly His Lys Thr Lys Asp Leu Gln Ala Ile Cys Gly Ile Ser
                260                 265                 270

Cys Asp Glu Leu Ser Ser Met Val Leu Glu Leu Arg Gly Leu Arg Thr
            275                 280                 285

Ile Val Thr Thr Leu Gln Asp Ser Ile Arg Lys Val Thr Glu Glu Asn
        290                 295                 300
```

```
Lys Glu Leu Ala Asn Glu Leu Arg Arg Pro Pro Leu Cys Tyr His Asn
305                 310                 315                 320

Gly Val Gln Tyr Arg Asn Asn Glu Glu Trp Thr Val Asp Ser Cys Thr
            325                 330                 335

Glu Cys His Cys Gln Asn Ser Val Thr Ile Cys Lys Lys Val Ser Cys
                340                 345                 350

Pro Ile Met Pro Cys Ser Asn Ala Thr Val Pro Asp Gly Glu Cys Cys
                355                 360                 365

Pro Arg Cys Trp Pro Ser Asp Ser Ala Asp Asp Gly Trp Ser Pro Trp
370                 375                 380

Ser Glu Trp Thr Ser Cys Ser Thr Ser Cys Gly Asn Gly Ile Gln Gln
385                 390                 395                 400

Arg Gly Arg Ser Cys Asp Ser Leu Asn Asn Arg Cys Glu Gly Ser Ser
            405                 410                 415

Val Gln Thr Arg Thr Cys His Ile Gln Glu Cys Asp Lys Arg Phe Lys
                420                 425                 430

Gln Asp Gly Gly Trp Ser His Trp Ser Pro Trp Ser Ser Cys Ser Val
            435                 440                 445

Thr Cys Gly Asp Gly Val Ile Thr Arg Ile Arg Leu Cys Asn Ser Pro
450                 455                 460

Ser Pro Gln Met Asn Gly Lys Pro Cys Glu Gly Glu Ala Arg Glu Thr
465                 470                 475                 480

Lys Ala Cys Lys Lys Asp Ala Cys Pro Ile Asn Gly Gly Trp Gly Pro
                485                 490                 495

Trp Ser Pro Trp Asp Ile Cys Ser Val Thr Cys Gly Gly Gly Val Gln
                500                 505                 510

Lys Arg Ser Arg Leu Cys Asn Asn Pro Ala Pro Gln Phe Gly Gly Lys
            515                 520                 525

Asp Cys Val Gly Asp Val Thr Glu Asn Gln Ile Cys Asn Lys Gln Asp
    530                 535                 540

Cys Pro Ile Asp Gly Cys Leu Ser Asn Pro Cys Phe Ala Gly Val Lys
545                 550                 555                 560

Cys Thr Ser Tyr Pro Asp Gly Ser Trp Lys Cys Gly Ala Cys Pro Pro
                565                 570                 575

Gly Tyr Ser Gly Asn Gly Ile Gln Cys Thr Asp Val Asp Glu Cys Lys
            580                 585                 590

Glu Val Pro Asp Ala Cys Phe Asn His Asn Gly Glu His Arg Cys Glu
                595                 600                 605

Asn Thr Asp Pro Gly Tyr Asn Cys Leu Pro Cys Pro Pro Arg Phe Thr
            610                 615                 620

Gly Ser Gln Pro Phe Gly Gln Gly Val Glu His Ala Thr Ala Asn Lys
625                 630                 635                 640

Gln Val Cys Lys Pro Arg Asn Pro Cys Thr Asp Gly Thr His Asp Cys
                645                 650                 655

Asn Lys Asn Ala Lys Cys Asn Tyr Leu Gly His Tyr Ser Asp Pro Met
                660                 665                 670

Tyr Arg Cys Glu Cys Lys Pro Gly Tyr Ala Gly Asn Gly Ile Ile Cys
            675                 680                 685

Gly Glu Asp Thr Asp Leu Asp Gly Trp Pro Asn Glu Asn Leu Val Cys
            690                 695                 700

Val Ala Asn Ala Thr Tyr His Cys Lys Lys Asp Asn Cys Pro Asn Leu
705                 710                 715                 720
```

```
Pro Asn Ser Gly Gln Glu Asp Tyr Asp Lys Asp Gly Ile Gly Asp Ala
                725                 730                 735

Cys Asp Asp Asp Asp Asn Asp Lys Ile Pro Asp Arg Asp Asn
        740                 745                 750

Cys Pro Pro His Tyr Asn Pro Ala Gln Tyr Asp Tyr Asp Arg Asp Asp
        755                 760                 765

Val Gly Asp Arg Cys Asp Asn Cys Pro Tyr Asn His Asn Pro Asp Gln
        770                 775                 780

Ala Asp Thr Asp Asn Asn Gly Glu Gly Asp Ala Cys Ala Ala Asp Ile
785                 790                 795                 800

Asp Gly Asp Gly Ile Leu Asn Glu Arg Asp Asn Cys Gln Tyr Val Tyr
                805                 810                 815

Asn Val Asp Gln Arg Asp Thr Asp Met Asp Gly Val Gly Asp Gln Cys
                820                 825                 830

Asp Asn Cys Pro Leu Glu His Asn Pro Asp Gln Leu Asp Ser Asp Ser
                835                 840                 845

Asp Arg Ile Gly Asp Thr Cys Asp Asn Asn Gln Asp Ile Asp Glu Asp
        850                 855                 860

Gly His Gln Asn Asn Leu Asp Asn Cys Pro Tyr Val Pro Asn Ala Asn
865                 870                 875                 880

Gln Ala Asp His Asp Lys Asp Gly Lys Gly Asp Ala Cys Asp His Asp
                885                 890                 895

Asp Asp Asn Asp Gly Ile Pro Asp Asp Lys Asp Asn Cys Arg Leu Val
                900                 905                 910

Pro Asn Pro Asp Gln Lys Asp Ser Asp Gly Asp Gly Arg Gly Asp Ala
        915                 920                 925

Cys Lys Asp Asp Phe Asp His Asp Ser Val Pro Asp Ile Asp Ile
    930                 935                 940

Cys Pro Glu Asn Val Asp Ile Ser Glu Thr Asp Phe Arg Arg Phe Gln
945                 950                 955                 960

Met Ile Pro Leu Asp Pro Lys Gly Thr Ser Gln Asn Asp Pro Asn Trp
                965                 970                 975

Val Val Arg His Gln Gly Lys Glu Leu Val Gln Thr Val Asn Cys Asp
            980                 985                 990

Pro Gly Leu Ala Val Gly Tyr Asp Glu Phe Asn Ala Val Asp Phe Ser
        995                 1000                1005

Gly Thr Phe Phe Ile Asn Thr Glu Arg Asp Asp Asp Tyr Ala Gly
    1010                1015                1020

Phe Val Phe Gly Tyr Gln Ser Ser Ser Arg Phe Tyr Val Val Met
    1025                1030                1035

Trp Lys Gln Val Thr Gln Ser Tyr Trp Asp Thr Asn Pro Thr Arg
    1040                1045                1050

Ala Gln Gly Tyr Ser Gly Leu Ser Val Lys Val Asn Ser Thr
    1055                1060                1065

Thr Gly Pro Gly Glu His Leu Arg Asn Ala Leu Trp His Thr Gly
    1070                1075                1080

Asn Thr Pro Gly Gln Val Thr Leu Trp His Asp Pro Arg His
    1085                1090                1095

Ile Gly Trp Lys Asp Phe Thr Ala Tyr Arg Trp Arg Leu Ser His
    1100                1105                1110

Arg Pro Lys Thr Gly Phe Ile Arg Val Val Met Tyr Glu Gly Lys
    1115                1120                1125

Lys Ile Met Ala Asp Ser Gly Pro Ile Tyr Asp Lys Thr Tyr Ala
```

```
                1130                1135                1140
Gly Gly Arg Leu Gly Leu Phe  Val Phe Ser Gln Glu  Met Val Phe
            1145                1150                1155

Phe Ser Asp Leu Lys Tyr Glu  Cys Arg Asp Pro
            1160                1165

<210> SEQ ID NO 8
<211> LENGTH: 547
<212> TYPE: DNA
<213> ORGANISM: Artificial Sequence
<220> FEATURE:
<223> OTHER INFORMATION: Homo sapiens

<400> SEQUENCE: 8
agcatctgat gcacaaaata gagtggtggt tgcttctttc cacacaggta ccccataata      60
cacaattttt cgctccctcc tccacaggtg acagaacagt tgcagagccg gatccttgtg     120
atcacaccat caccacatgt cacagaacaa gaagacccct tgcgggcggc cccggtgagt     180
tcaaagatgt caaacacgct gttgtctccg ccagactctg gaatgcggtt ggtgccacac     240
acatgcatca ggaacaggac gcctagtccc caggccagcc ccatctgcag aaaagaccca     300
tggaaaggaa cagtctgtta gtctgtcagc tattatgtct ggtggcgcgc gcggcagcaa     360
cgagtactgc tcagactaca ctgccctcca ccgttaacag caccgcaacg ggagttacct     420
ctgactctta tcagaataca acaactcaag ctgcctgcat cttcttctgc cgctgcctta     480
agtcttccat ctgcgtcagc cgtgcgagcc caatcttcac gctcattttc agacacatac     540
cctaccg                                                              547

<210> SEQ ID NO 9
<211> LENGTH: 547
<212> TYPE: DNA
<213> ORGANISM: Artificial Sequence
<220> FEATURE:
<223> OTHER INFORMATION: Homo sapiens

<400> SEQUENCE: 9
tcgtagacta cgtgttttat ctcaccacca acgaagaaag ctgtgtccat gactgtgacc      60
gtgttaaaaa ggggtattat aggtctccac tgtcttgtca acgtctcggc ctaggaacac     120
tagtgtggta gtggtgtaca gtgtcttgtt cttctgggga acgcccgccg gggccactca     180
agtttctaca gtttgtgcga caacagaggc ggtctgagac cttacgccaa ccacggtgtg     240
tgtacgtagt ccttgtcctg cggatcaggg gtccggtcgg ggtagacgtc ttttctgggt     300
acctttcctt gtcagacaat cagacagtcg ataatacaga ccaccgcgcg cgccgtcgtt     360
gctcatgacg agtctgatgt gacgggaggt ggcaattgtc gtggcgttgc cctcaatgga     420
gactgagaat agtcttatgt tgttgagttc gacggacgta aagaagacg gcgacggaat     480 tcagaaggta gacgcagtcg gcacgctcgg gttagaagtg cgagtaaaag tctgtctatg     540
ggatggc                                                              547

<210> SEQ ID NO 10
<211> LENGTH: 98
<212> TYPE: PRT
<213> ORGANISM: Artificial Sequence
<220> FEATURE:
<223> OTHER INFORMATION: Homo sapiens

<400> SEQUENCE: 10

Ala Asp Ser Ala Cys Phe Leu Thr Thr Thr Ala Glu Lys Trp Val Pro
```

```
1               5                   10                  15
Val Gly Tyr Tyr Val Thr Val Trp Leu Lys Glu Ser Gly Gly Gly Cys
            20                  25                  30

Thr Val Ser Cys Asn Cys Leu Arg Ile Arg Thr Ile Val Gly Asp Gly
        35                  40                  45

Cys Thr Val Ser Cys Ser Ser Gly Lys Arg Ala Ala Gly Thr Leu Glu
        50                  55                  60

Phe Ile Asp Phe Val Ser Asn Asp Gly Gly Ser Glu Pro Ile Arg Asn
65                      70                  75                  80

Thr Gly Cys Val His Met Leu Phe Leu Val Gly Leu Gly Trp Ala Leu
                85                  90                  95

Gly Met

<210> SEQ ID NO 11
<211> LENGTH: 6
<212> TYPE: PRT
<213> ORGANISM: Homo sapiens

<400> SEQUENCE: 11

Cys Ser Val Thr Cys Gly
1               5
```